US 7,521,054 B2

(12) United States Patent
Pastan et al.

(10) Patent No.: US 7,521,054 B2
(45) Date of Patent: Apr. 21, 2009

(54) REDUCTION OF THE NONSPECIFIC ANIMAL TOXICITY OF IMMUNOTOXINS BY MUTATING THE FRAMEWORK REGIONS OF THE FV TO LOWER THE ISOELECTRIC POINT

(75) Inventors: Ira H. Pastan, Potomac, MD (US); Masanori Onda, Rockville, MD (US); Satoshi Nagata, Rockville, MD (US); Yasuo Tsutsumi, Mino (JP); James J. Vincent, Takoma Park, MD (US); Robert J. Kreitman, Potomac, MD (US); George Vasmatzis, Rochester, MN (US); Byungkook Lee, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 484 days.

(21) Appl. No.: 10/416,129

(22) PCT Filed: Nov. 16, 2001

(86) PCT No.: PCT/US01/43602

§ 371 (c)(1),
(2), (4) Date: Dec. 18, 2003

(87) PCT Pub. No.: WO02/40545

PCT Pub. Date: May 23, 2002

(65) Prior Publication Data

US 2004/0091489 A1    May 13, 2004

Related U.S. Application Data

(60) Provisional application No. 60/249,805, filed on Nov. 17, 2000.

(51) Int. Cl.
*A61K 47/48* (2006.01)
*C07K 16/18* (2006.01)
*C07K 16/28* (2006.01)

(52) U.S. Cl. ............... 424/178.1; 435/69.7; 435/328; 530/391.1

(58) Field of Classification Search ........................ None
See application file for complete search history.

(56) References Cited

OTHER PUBLICATIONS

Onda et al. (J. Immunol. 163:6072-6077 (Dec. 1, 1999)).*
Search output from ATCC website for SS1 antibody/hybridoma (pp. 1-2).*
Search output from ATCC website for B3 antibody/hybridoma (pp. 1-2).*
Fundamental Immunology 242 (William E. Paul, M.D. ed., 3d ed. 1993).*
Lederman et al (Molecular Immunology 28:1171-1181, 1991).*
Li et al (Proc. Natl. Acad. Sci. USA 77:3211-3214, 1980).*
Katz et al. (J. Exp. Med. 180:925-932 (1994).*
Colcher et al., (Quarterly J. Nucl. Med. 42(4):225-241 (1998).*
Pavlinkova et al. (Nuc. Med. & Biol. 26:27-34 (1999).*
Idziorek et al. (Infect. Immun. 58(5): 1415-1420 (1990)).*
Onda et al. (J. Immunol. 163:6072-6077 (1999)).*
Chowdhury et al. (PNAS 95:669-674 (1998)).*
Brinkman et al. (PNAS 90:7538-7542 (1993)).*
Vajdos et al. (2002) J. Mol. Biol. 320, 415-428.*
Wu et al. J. Mol. Biol. (1999) 294, 151-162.*
Coleman (Research in Immunol. 145:33-36 (1994)).*
Studnicka (Prot. Engineer. 7(6):805-814 (1994)).*
Brinkmann, U. et al.; "A Recombinant Immunotoxin Containing a Disulfide-Stabilized Fv Fragment"; 1993, *PNAS*, vol. 90, pp. 7538-7542.
Chaudhary, Vijay K. et al.; "" Isolation of a high-affinity stable single-chain Fv specific for mesothelin from DNA-immunized mice by phage display and construction of a recombinant immunotoxin with anti-tumor activity; 1998, *PNAS*, vol. 95, pp. 669-674.
Kobayashi, Hisataka et al; "The Pharmacokinetic Characteristics of Glycolated Humanized Anti-Tac Fabs Are Determined by Their Isoelectric Points"; 1999, *Cancer Research*, vol. 59, pp. 422-430.
Kreitman, Robert J. et al.; "Immunotoxins for targeted cancer therapy"; 1998, *Advanced Drug Delivery Reviews*, vol. 31, pp. 53-88.
Ll, Tianyong et al.; "Coexpression of *cyt1Aa* of *Bacillus thuringiensis* subsp. *israelensis* with *Bacillus sphaericus* Binary Toxin Gene in Acrystalliferous Strain of *B. thuringiensis*"; 2000, *Current Microbiology*, vol. 40, pp. 322-326.
Onda, Masanori et al.; "Reduction of the Nonspecific Animal Toxicity of Anti-Tac(Fv)-PE38 by Mutations in the Framework Regions of the Fv Which Lower the Isoelectric Point"; 1999, *The Journal of Immunology*, pp. 6072-6077.

(Continued)

*Primary Examiner*—David J. Blanchard
*Assistant Examiner*—Lynn Bristol
(74) *Attorney, Agent, or Firm*—Townsend and Townsend and Crew LLP

(57) ABSTRACT

The invention provides recombinant immunotoxins that have been modified from a parental immunotoxin to lower liver toxicity. The immunotoxins are created by specifically mutating charged residues in the framework regions of the heavy chain, the light chain, or both, of the antibody portion or antigen-binding fragment thereof of the parental immunotoxin to reduce the pI of the antibody or fragment. In preferred forms, the antibody portion of the parental is an anti-Tac, anti-mesothelin, or anti-LewisY antigen antibody or antigen-binding fragment, and in particularly preferred forms the antibody portion is an M16 dsFv, a St6 dsFv or a Mt9 dsFv, or a sequence that has at least 90% sequence identity to one of these molecules but retain the particular mutations that lower pI without affecting antibody activity. The invention further provides nucleic acids encoding the recombinant immunotoxins of the invention, expression cassettes comprising the nucleic acids, and host cells comprising the expression cassettes. The invention also provides a method for killing a cell comprising an antigen on the surface of the cell, the method comprising contacting the cell with a recombinant immunotoxin of the invention that has an antibody or antigen-binding fragment thereof that binds specifically to the antigen on the surface of the cell, and uses of immunotoxins of the invention for the manufacture of medicaments.

8 Claims, 10 Drawing Sheets

OTHER PUBLICATIONS

Pastan, Ira et al.; "Recombinant Toxins for Cancer Treatment"; 1991, *Science*, vol. 254, pp. 1173-1177.

Reiter, Yoram et al.; "Stabilization of the Fv Fragments in Recombinant Immunotoxins by Disulfide Bonds Engineered into Conserved Framework Regions"; 1994, *Biochemistry*, vol. 33, pp. 5451-5459.

Yokota, Takashi et al.; "Rapid Tumor Penetration of a Single-Chain Fv and Comparison with Other Immunoglobulin Forms"; 1992, *Cancer Research*, vol. 52, pp. 3402-3408.

Bird, Robert E. et al.; "Single-Chain Antigen-Binding Proteins"; 1998, *Science*, vol. 242, pp. 423-426.

Chaudhary, Vijay K. et al.; "A recombinant immunotoxin consisting of two antibody variable domains fused to *Pseudomonas exotoxin*"; 1989, *Nature*, vol. 339, pp. 394-397.

Chowdhury, Partha S. et al.; "Isolation of a high-affinity stable single-chain Fv specific for mesothelin from DNA-immunized mice by phage display and construction of a recombinant immunotoxin with anti-tumor activity"; 1998, *PNAS*, vol. 95, pp. 669-674.

Kim, L.S. et al.; "Acylation with Glycolate Lowers pI of Anti-Tac dsFv and Reduces Renal Uptake of Its Tc-99 Label"; 1997, *J. Label. Compd XL*, vol. 40, pp. 422-425.

* cited by examiner

FIG. 2.

| FIG. 2A. | FIG. 2B. |
|---|---|
| FIG. 2C. | FIG. 2D. |

FIG. 2B.

|  | FR3 |  |  | CDR3 |  | FR4 |
|---|---|---|---|---|---|---|
|  | 6 | 7 | 8 |  | 9 | 1 |
|  | 7890123456789 | 0123456 | 78901234567 8 | 901234 5ABCDEF67 | 89012 3456789 |
|  | GVPARFSGSGSGT | SYSLTI | SRMEAEDAATYYC | HQRSTYP------LT | FGCGTKLELK |
|  | GVPARFSGSGSGT | DYSLTI | SRMEAEDAATYYC | HQRSTYP------LT | FGCGTKLELK |
|  | GVPARFSGSGSGT | DYSLTI | SNMEAEDAATYYC | HQRSTYP------LT | FGCGTELELE |
|  | GVPDRFSGSGSGT | SYSLTI | SSVEAEDDATYYC | QQWSKHP------LT | FGCGTKLEIK |
|  | GVPDRFSGSGSGT | NSYSLTI | SSVEEEDDATYYC | QQWSKHP------LT | FGCGTKLEIK |
|  | GVPDRFSGSGSGT | DFTLKI | SRVEAEDLGVYYC | FQGSHVP------FT | FGCGTKLEIK |
|  | GVPDRFSGSGSGT | DFTLTI | SSVEAEDLGVYYC | FQGSHVP------FT | FGCGTELEID |
|  | GVP RFSGSGSGT DFSLTISS | | EAED A YYC | ---------- | FGGGTKLEIKKRA |
|  | A | YT | V AT | | |
|  | D | | L | | |
|  | S | S | K RMQ GV F | | A LG |
|  | | | L | | |
|  | T | | N V | | S |
|  | | | P | | |
|  | I | N N | SD I D | | |
|  | | | H P F | | |
|  | | | E | | |
|  | | R Q | FS Q S | | |
|  | | S | M | | |
|  | | | I | | |
|  | V | R Q | R T KT T | | L |
|  | | S | M | | T |
|  | SK | IS Y RA | T V TH | | K |
|  | | | G Y VE | | |
|  | | | D | | |

| VL | FR1 | | | CDR1 | | FR2 | | CDR2 |
|---|---|---|---|---|---|---|---|---|
| Kabat | 1234567890123 | 2 | 3 | 4567ABCDEF8901234 | | 5678901234567 | 4 | 0123456 |
| | 1234567890123 | | | | | | 89 | |
| dsAT | DIVLTQSPAIMSASPGEKVTITC | | | SASS-------SISYMH | | MFQQKPGTSPKLWIY | | TTSNLAS |
| M1 | DIELTQSPAIMSASPGEKVTITC | | | SASS-------SISYMH | | MFQQKPGTSPKLWIY | | TTSNLAS |
| M16 | DIELTQSPAIMSASPGEQVTITC | | | SASS-------SISYMH | | MFQQKPGTSPQLWIY | | TTSNLAS |
| SS1 | DIELTQSPAIMSASPGEKVTMTC | | | SASS-------SVSYMH | | WYQQKSGTSPKRWIY | | DTSKLAS |
| ST6 | DIELTQDPAIMSASPGEKVTMTC | | | SASS-------SVSYMH | | WYQQKSGTSPKRWIY | | DTSKLAS |
| dsB3 | DVVMTQSPLSLPVSLGDQASISC | | | RSSQIIVH-SNGNTYLE | | WYLQKPGQSPKLLIY | | KVSNRFS |
| Mt9 | DVEMTQSPLSLPVSLGDQASISC | | | RSSQIIVH-SNGNTYLE | | WYLQKPGQSPKLLIY | | KVSNRFS |
| 50-100 | DIVMTQSP SLS S G VTISC | | | | | WYQQKPG SPKLLIY | | |
| 30-50 | L A M V L EK T | | | | | Q | | |
| | A DR | | | | | | | |
| 20-30 | T SI A P ASM | | | | | L S RW | | |
| 10-20 | QVQ L P TV QQ | | | | | TP Q | | |
| | | | | | | K | | |
| 5-10 | E L TKF T L | | | | | F R DGTVR V | | |
| | T S | | | | | S | | |
| 3-5 | S AT T I | | | | | L QE P K | | |
| 2-3 | NNEI AH NYM ISKP | | | | | H E T S | | |
| | K T | | | | | | | |
| 1-2 | L VI DEPLV S G VN | | | | | KE WAAI A H | | |
| | QFYT T F | | | | | E HFG F | | |
| | | | | | | N | | |

← Percent Frequency →

| FR3 | | | CDR3 | | FR4 | |
|---|---|---|---|---|---|---|
| 7 | 8 | 9 | | 10 | | 11 |
| 6789012345678901234 | | | 567890ABCDEFGHIJK12 | | 3456789 | 0123 |
| KATLTADKSSSTAYMQLSSLTFEDSAVYYCAR | | | GGGVF--------------DY | | MGQGTTLTVSS | |
| KATLTADKSSSTAYMQLSSLTFEDSAVYYCAR | | | GGGVF--------------DY | | MGQGTTLTVSS | |
| KATLTADDSSSTAYMQLSSLTFEDSAVYYCAR | | | GGGVF--------------DY | | MGQGTTLTVSS | |
| KATLTVDKSSSTAYMDLLSLTSEDSAVYFCAR | | | GGYDGRGF------------DY | | MGQGTTVTVSS | |
| KATLTVDKSQSTAYMDLLNLTNEDSAVFCAR | | | GGYDGRGF------------DY | | MGQGTTVTVSS | |
| RFTISRDNARNTLYLQMSRLKSEDTAIYYCAR | | | GLAWGAWF------------AY | | MGQGTLVTVS | |
| RFTISRDNARNTLYLQMSRLKSEDTAIYYCAR | | | GLAWGAWF------------AY | | MGQGTLVTV | |
| K TLT D SSSTAYMQLSSLTSEDSAVYYCAR | | | | | MGQGT VTVSS | |
| RA ISV K L M T | | | | | TL | |
| F RT KN L N | | | | | L A | |
|      N | | | | | S | |
| S P QVF E R RT TF | | | | | A | |
|   A A   M | | | | | | |
|        I | | | | | | |
| TI K QI K NVK D L T | | | | | T | |
| L   A Q | | | | | | |
| I V ED A IT VS | | | | | | |
| F R | | | | | | |
| A L SF K N G K | | | | | | |
|  S     G | | | | | | |
| G M TNYHFHVHT D A MT | | | | | | |
|        R R   S | | | | | | |
|          G   G | | | | | | |

SEQUENCE LISTING

<160> NUMBER OF SEQ ID NOS: 47

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence:V-L chain of
      disulfide stabilized anti-Tac Fv (dsAT)

<400> SEQUENCE: 1

Gln Ile Val Leu Thr Gln Ser Pro Ala Ile Met Ser Ala Ser Pro Gly
 1               5                  10                  15

Glu Lys Val Thr Ile Thr Cys Ser Ala Ser Ser Ser Ile Ser Tyr Met
                20                  25                  30

His Trp Phe Gln Gln Lys Pro Gly Thr Ser Pro Lys Leu Trp Ile Tyr
            35                  40                  45

Thr Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Cys Gly Thr Lys Leu Glu Leu Lys
                    100                 105

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence:V-L chain of
      anti-Tac Fv in which selected neutral residues
      mutated to acidic residues (M1)

<400> SEQUENCE: 2

Asp Ile Glu Leu Thr Gln Ser Pro Ala Ile Met Ser Ala Ser Pro Gly
 1             5               10               15

Glu Lys Val Thr Ile Thr Cys Ser Ala Ser Ser Ser Ile Ser Tyr Met
           20               25              30

His Trp Phe Gln Gln Lys Pro Gly Thr Ser Pro Lys Leu Trp Ile Tyr
        35               40              45

Thr Thr Ser Asn Leu Ala Ser Gly Val Pro Ala Arg Phe Ser Gly Ser
    50               55              60

Gly Ser Gly Thr Asp Tyr Ser Leu Thr Ile Ser Arg Met Glu Ala Glu
65                 70              75               80

Asp Ala Ala Thr Tyr Tyr Cys His Gln Arg Ser Thr Tyr Pro Leu Thr
           85               90              95

Phe Gly Cys Gly Thr Lys Leu Glu Leu Lys
                    100                 105

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence:V-L chain of
      anti-Tac Fv in which neutral and basic residues
      mutated to acidic residues (M16)

<400> SEQUENCE: 3

Asp Ile Glu Leu Thr Gln Ser Pro Ala Ile Met Ser Ala Ser Pro Gly
 1             5               10               15

Glu Gln Val Thr Ile Thr Cys Ser Ala Ser Ser Ser Ile Ser Tyr Met
           20               25              30

His Trp Phe Gln Gln Lys Pro Gly Thr Ser Pro Gln Leu Trp Ile Tyr
        35               40              45

Thr Thr Ser Asn Leu Ala Ser Gly Val Pro Ala Arg Phe Ser Gly Ser
    50               55              60

Gly Ser Gly Thr Asp Tyr Ser Leu Thr Ile Ser Asn Met Glu Ala Glu
65                 70              75               80

Asp Ala Ala Thr Tyr Tyr Cys His Gln Arg Ser Thr Tyr Pro Leu Thr
           85               90              95

Phe Gly Cys Gly Thr Glu Leu Glu Leu Glu
                    100                 105

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence:V-L chain of
      anti-mesothelin Fv (SS1)

<400> SEQUENCE: 4

```
Asp Ile Glu Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Cys Gly Thr Lys Leu Glu Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence:V-L chain of
      anti-mesothelin Fv in which neutral and basic
      residues mutated to acidic residues (ST6)

<400> SEQUENCE: 5

Asp Ile Glu Leu Thr Gln Asp Pro Ala Ile Met Ser Ala Ser Pro Gly
 1               5                  10                  15

Glu Gln Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Asp Arg Phe Ser Gly Ser
        50                  55                  60

Gly Ser Gly Asn Ser Tyr Ser Leu Thr Ile Ser Ser Val Glu Glu Glu
65                  70                  75                  80

Asp Asp Ala Thr Tyr Tyr Cys Gln Gln Trp Ser Lys His Pro Leu Thr
                85                  90                  95

Phe Gly Cys Gly Thr Lys Leu Glu Ile Glu
            100                 105

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence:V-L chain of
      disulfide stabilized anti-Y-Lewis B3 Fv (dsB3)

<400> SEQUENCE: 6

Asp Val Leu Met Thr Gln Ser Pro Leu Ser Leu Pro Val Ser Leu Gly
 1               5                  10                  15

Asp Gln Ala Ser Ile Ser Cys Arg Ser Ser Gln Ile Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Tyr Cys Phe Gln Gly
                    85                  90                  95

Ser His Val Pro Phe Thr Phe Gly Cys Gly Thr Lys Leu Glu Ile Lys
                100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence:V-L chain of
      anti-Y-Lewis B3 Fv in which neutral and basic
      residues mutated to acidic residues (Mt9)

<400> SEQUENCE: 7

```
Asp Val Glu Met Thr Gln Ser Pro Leu Ser Leu Pro Val Ser Leu Gly
 1               5                  10                  15

Asp Gln Ala Ser Ile Ser Cys Arg Ser Ser Gln Ile Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
 65                  70                  75                  80

Ser Ser Val Glu Ala Glu Asp Leu Gly Val Tyr Tyr Cys Phe Gln Gly
                    85                  90                  95

Ser His Val Pro Phe Thr Phe Gly Cys Gly Thr Asp Leu Glu Ile Asp
                100                 105                 110
```

<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence:V-H chain of
      disulfide stabilized anti-Tac Fv (dsAT)

<400> SEQUENCE: 8

```
Gln Val His Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Ser Tyr
                20                  25                  30

Arg Met His Trp Val Lys Gln Arg Pro Gly Gln Cys Leu Glu Trp Ile
            35                  40                  45

Gly Tyr Ile Asn Pro Ser Thr Gly Tyr Thr Glu Tyr Asn Gln Lys Phe
        50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Phe Glu Asp Ser Ala Val Tyr Tyr Cys
                    85                  90                  95

Ala Arg Gly Gly Gly Val Phe Asp Tyr Trp Gly Gln Gly Thr Thr Leu
                100                 105                 110

Thr Val Ser
        115
```

<210> SEQ ID NO 9
<211> LENGTH: 116

```
<212> TYPE: PRT
<213> ORGANISM: Artificial Sequence
<220> FEATURE:
<223> OTHER INFORMATION: Description of Artificial Sequence:V-H chain of
      anti-Tac Fv in which selected neutral residues
      mutated to acidic residues (M1)

<400> SEQUENCE: 9

Glu Val Gln Leu Val Glu Ser Gly Ala Glu Leu Ala Lys Pro Gly Ala
  1               5                  10                  15

Ser Val Lys Met Ser Cys Lys Ala Ser Gly Tyr Thr Phe Thr Ser Tyr
             20                  25                  30

Arg Met His Trp Val Lys Gln Arg Pro Glu Gln Cys Leu Glu Trp Ile
         35                  40                  45

Gly Tyr Ile Asn Pro Ser Thr Gly Tyr Thr Glu Tyr Asn Gln Lys Phe
     50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Phe Glu Asp Ser Ala Val Tyr Tyr Cys
                 85                  90                  95

Ala Arg Gly Gly Gly Val Phe Asp Tyr Trp Gly Gln Gly Thr Thr Leu
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence:V-H chain of
      anti-Tac Fv in which neutral and basic residues
      mutated to acidic residues (M16)

<400> SEQUENCE: 10

Glu Val Gln Leu Val Glu Ser Gly Ala Glu Leu Ala Glu Pro Gly Ala
  1               5                  10                  15

Ser Val Lys Met Ser Cys Lys Ala Ser Gly Tyr Thr Phe Thr Ser Tyr
             20                  25                  30

Arg Met His Trp Val Lys Gln Arg Pro Glu Gln Cys Leu Glu Trp Ile
         35                  40                  45

Gly Tyr Ile Asn Pro Ser Thr Gly Tyr Thr Glu Tyr Asn Gln Lys Phe
     50                  55                  60

Lys Asp Lys Ala Thr Leu Thr Ala Asp Asp Ser Ser Ser Thr Ala Tyr
 65                  70                  75                  80

Met Gln Leu Ser Ser Leu Thr Phe Glu Asp Ser Ala Val Tyr Tyr Cys
                 85                  90                  95

Ala Arg Gly Gly Gly Val Phe Asp Tyr Trp Gly Gln Gly Thr Thr Leu
            100                 105                 110

Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence:V-H chain of
      anti-mesothelin Fv (SS1)

<400> SEQUENCE: 11
```

```
Gln Val Gln Leu Gln Gln Ser Gly Pro Glu Leu Glu Lys Pro Gly Ala
1               5                   10                  15

Ser Val Lys Leu Ser Cys Lys Ala Ser Gly Tyr Ser Phe Thr Gly Tyr
            20                  25                  30

Thr Met Asn Trp Val Lys Gln Ser His Gly Lys Cys Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65              70                  75                  80

Met Asp Leu Leu Ser Leu Thr Ser Glu Asp Ser Ala Val Tyr Phe Cys
            85                  90                  95

Ala Arg Gly Gly Tyr Asp Gly Arg Gly Phe Asp Tyr Trp Gly Gln Gly
            100                 105                 110

Thr Thr Val Thr Val Ser Ser
        115
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence:V-H chain of
      anti-mesothelin Fv in which neutral and basic
      residues mutated to acidic residues (ST6)

<400> SEQUENCE: 12

```
Glu Val Gln Leu Gln Gln Ser Gly Pro Glu Leu Glu Gln Pro Gly Ala
1               5                   10                  15

Ser Val Lys Leu Ser Cys Lys Ala Ser Gly Tyr Ser Phe Thr Gly Tyr
            20                  25                  30

Thr Met Asn Trp Val Lys Gln Ser His Gly Lys Cys Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Gln Ser Thr Ala Tyr
65              70                  75                  80

Met Asp Leu Leu Asn Leu Thr Asn Glu Asp Ser Ala Val Tyr Phe Cys
            85                  90                  95

Ala Arg Gly Gly Tyr Asp Gly Arg Gly Phe Asp Tyr Trp Gly Gln Gly
            100                 105                 110

Thr Thr Val Thr Val Ser Ser
        115
```

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence:V-H chain of
      disulfide stabilized anti-Y-Lewis B3 Fv (dsB3)

<400> SEQUENCE: 13

```
Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Cys Leu Glu Trp Val
```

```
                    35                  40                  45
Ala Tyr Ile Ser Asn Asp Asp Ser Ser Ala Ala Tyr Ser Asp Thr Val
         50                  55                  60
Lys Gly Arg Phe Thr Ile Ser Arg Asp Asn Ala Arg Asn Thr Leu Tyr
 65                  70                  75                  80
Leu Gln Met Ser Arg Leu Lys Ser Glu Asp Thr Ala Ile Tyr Tyr Cys
                 85                  90                  95
Ala Arg Gly Leu Ala Trp Gly Ala Trp Phe Ala Tyr Trp Gly Gln Gly
            100                 105                 110
Thr Leu Val Thr Val Ser
        115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence:V-H chain of
      anti-Y-Lewis B3 Fv in which neutral and basic
      residues mutated to acidic residues (Mt9)

<400> SEQUENCE: 14

Asp Val Lys Leu Val Glu Ser Gly Gly Gly Leu Val Gln Pro Gly Gly
 1               5                  10                  15
Ser Leu Lys Leu Ser Cys Ala Thr Ser Gly Phe Thr Phe Ser Asp Tyr
             20                  25                  30
Tyr Met Tyr Trp Val Arg Gln Thr Pro Glu Lys Cys Leu Glu Trp Val
         35                  40                  45
Ala Tyr Ile Ser Asn Asp Asp Ser Ser Ala Ala Tyr Ser Asp Thr Val
     50                  55                  60
Lys Gly Arg Phe Thr Ile Ser Arg Asp Asn Ala Arg Asn Thr Leu Tyr
 65                  70                  75                  80
Leu Gln Met Ser Arg Leu Lys Ser Glu Asp Thr Ala Ile Tyr Tyr Cys
                 85                  90                  95
Ala Arg Gly Leu Ala Trp Gly Ala Trp Phe Ala Tyr Trp Gly Gln Gly
            100                 105                 110
Thr Leu Val Thr Val Ser
        115

<210> SEQ ID NO 15
<211> LENGTH: 318
<212> TYPE: DNA
<213> ORGANISM: Artificial Sequence
<220> FEATURE:
<223> OTHER INFORMATION: Description of Artificial Sequence:M16 VL Fv

<400> SEQUENCE: 15
gacatcgaac tcacccagtc tccagcaatc atgtctgcat ctccagggga gcaagtcacc      60
ataacctgca gtgccagctc aagtataagt tacatgcact ggttccagca gaagccaggc    120
acttctcccc agctatggat ttataccaca tccaacctgg cttctggagt ccctgctcgc    180
ttcagtggca gtggatccgg gaccgattac tctctcacaa tttcgaatat ggaggctgaa    240
gatgctgcca cttattactg ccatcaaagg agtacttacc cactcacgtt cggttgcggg    300
accgagctgg aactcgaa                                                  318

<210> SEQ ID NO 16
<211> LENGTH: 348
<212> TYPE: DNA
```

<213> ORGANISM: Artificial Sequence
<220> FEATURE:
<223> OTHER INFORMATION: Description of Artificial Sequence:M16 VH Fv

<400> SEQUENCE: 16

```
gaggtccaac tggtggagtc tggggctgag ctcgcagaac ctggggcctc agtgaagatg      60
tcctgcaagg cttctggcta cacctttact agctacagga tgcactgggt aaaacagagg     120
cctgaacagt gtctggaatg gattggatat attaatccta gcactgggta tactgaatac     180
aatcagaagt tcaaggacaa ggccacattg actgcagacg attcctccag tactgcctac     240
atgcaactga gcagcctgac atttgaggac tctgcagtct attactgtgc aagagggggg     300
ggggtctttg actactgggg ccaaggaacc actctcacag tctcctcc                  348
```

<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence:St6 VL Fv

<400> SEQUENCE: 17

```
atggacatcg agctcactca ggatccagca atcatgtctg catctcccgg ggagcaggtc      60
accatgacct gcagtgccag ctcaagtgta agttacatgc actggtacca gcagaagtca     120
ggcacctccc ccaaaagatg gatttatgac acatccaaac tggcttctgg agtccccgat     180
cgcttcagtg gcagtgggtc tggaaactct tactctctca caatcagcag cgtggaggag     240
gaagatgatg ctacgtatta ctgccagcag tggtccaagc ccctctcac gttcggttgc     300 gggacaaagc ttgaaataga a                                                321
```

<210> SEQ ID NO 18
<211> LENGTH: 357
<212> TYPE: DNA
<213> ORGANISM: Artificial Sequence
<220> FEATURE:
<223> OTHER INFORMATION: Description of Artificial Sequence:St6 VH Fv

<400> SEQUENCE: 18

```
gaggtacaac tgcagcagtc tgggcctgag ctcgagcagc ctggcgcttc agtgaagtta      60
tcctgcaagg catctggtta ctcattcact ggctacacca tgaactgggt gaagcagagt     120
catggaaagt gccttgagtg gattggactt attactcctt acaatggtgc ttctagctac     180
aaccagaagt tcaggggcaa ggccacatta actgtagaca gtgtcacaaag tactgcctac     240 atggacctcc tcaatctgac aaatgaagac tctgcagtct atttctgtgc aaggggggggt     300 tacgacggga gggttttga ctactggggc caagggacca cggtcaccgt ctcctca        357
```

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence:Mt9 VL Fv

<400> SEQUENCE: 19

```
gacgtggaga tgacccagtc tccattgagt ttacctgtca gtcttggaga tcaagcctcc      60
atctcttgca gatctagtca gatcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaccatc     240
```

-continued

```
agcagtgtgg aggcggagga tctgggagtt tattactgct ttcaaggttc acatgttcca      300
ttcacgttcg gctgtgggac agatctggaa atagat                                336

<210> SEQ ID NO 20
<211> LENGTH: 354
<212> TYPE: DNA
<213> ORGANISM: Artificial Sequence
<220> FEATURE:
<223> OTHER INFORMATION: Description of Artificial Sequence:Mt9 VH Fv

<400> SEQUENCE: 20
gatgtgaagc tggtggagtc tggggggaggc ttagtgcagc ctggagggtc cctgaaactc      60
tcctgtgcaa cctctggatt cactttcagt gactattaca tgtattgggt tcgccagact     120
ccagagaagt gtctcgagtg ggtcgcatac attagtaatg atgatagttc cgccgcttat     180
tcagacactg taaagggccg gttcaccatc tccagagaca tgccaggaa cccctctac       240 ctgcaaatga gccgtctgaa gtctgaggac acagccatat attactgcgc aagaggactg     300
gcctggggag cctggtttgc ttactgggc caagggactc tggtcactgt ctcc            354

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence:M1 V-L Q1D
      primer

<400> SEQUENCE: 21
tgctggagac tgggtgagaa cgatatcaga gccgccgcca cccgagccgc caccgcccga     60
gccacc                                                                 66

<210> SEQ ID NO 22
<211> LENGTH: 64
<212> TYPE: DNA
<213> ORGANISM: Artificial Sequence
<220> FEATURE:
<223> OTHER INFORMATION: Description of Artificial Sequence:M1
      V-L Q1DL V3E primer

<400> SEQUENCE: 22
gattgctgga gactgggtga gttcgatatc agagccgccg ccacccgagc cgccaccgcc      60
cgag                                                                   64

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence:M1 V-L S70D
      primer

<400> SEQUENCE: 23
gctgattgtg agagagtaat cggtcccgga tccactgcca ctgaagcg                   48

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence:M1 V-L
      S100D primer
```

-continued

```
<400> SEQUENCE: 24
tttgagctcc agcttggtac catcaccgaa cgtgagtggg ta                    42

<210> SEQ ID NO 25
<211> LENGTH: 66
<212> TYPE: DNA
<213> ORGANISM: Artificial Sequence
<220> FEATURE:
<223> OTHER INFORMATION: Description of Artificial Sequence:M1 V-H Q1E
      primer

<400> SEQUENCE: 25
tgaggcccca ggttttgcta gctcagcccc agactgctgc agatggacct ccatatgtat   60
atctcc                                                             66

<210> SEQ ID NO 26
<211> LENGTH: 54
<212> TYPE: DNA
<213> ORGANISM: Artificial Sequence
<220> FEATURE:
<223> OTHER INFORMATION: Description of Artificial Sequence:M1 V-H Q6E
      primer

<400> SEQUENCE: 26
tgaggcccca ggttttgcta gctcagcccc agactcctgc agatggacct gcat         54

<210> SEQ ID NO 27
<211> LENGTH: 66
<212> TYPE: DNA
<213> ORGANISM: Artificial Sequence
<220> FEATURE:
<223> OTHER INFORMATION: Description of Artificial Sequence:M1 V-H
      Q1E+H3Q+Q5V+Q6E primer

<400> SEQUENCE: 27
tgaggcccca ggttttgcta gctcagcccc agactccacc agttggacct ccatatgtat   60
atctcc                                                             66

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:M1 V-H G42E
      primer

<400> SEQUENCE: 28
aatccattcc agaccctgtt caggtctctg ttttacccag tgcat                  45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence:M1 VL K18Q
      primer

<400> SEQUENCE: 29
ggcactgcag gttatggtga cttgctcccc tggagatgca gacat                  45

<210> SEQ ID NO 30
<211> LENGTH: 42
<212> TYPE: DNA
<213> ORGANISM: Artificial Sequence
<220> FEATURE:
```

-continued

<223> OTHER INFORMATION: Description of Artificial Sequence:Mi VL K45Q
      primer

<400> SEQUENCE: 30
ggatgtggta taaatccata gctggggaga agtgcctggc tt                                    42

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence:M1 VL R77N
      primer

<400> SEQUENCE: 31
ggcagcatct tcagcctcca tattcgaaat tgtgagagag taatcggt                              48

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence:M1 VL
      K103-107E primer

<400> SEQUENCE: 32
gttagcagcc gaattctatt cgagttccag ctcggtcccg caaccgaacg tgag                       54

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence:M1 VH K13E
      primer

<400> SEQUENCE: 33
catcttcact gaggccccag gttctgcgag ctcagcccca ga                                    42

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence:M1 VH K73D
      primer

<400> SEQUENCE: 34
gctcagttgc atgtaggcag tactggagga atcgtctgca gtcaa                                 45

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence:M1 VL E100C
      primer

<400> SEQUENCE: 35
gccgccctcg ggacctgaat tctatttgag ctccagcttg gtcccgcaac cgaacgtgag                 60
tgggta                                                                            66

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence:M1 VH G44C
     primer

<400> SEQUENCE: 36
atatccaatc cattccagac actgttcagg cctctgtttt acccagtgca t    51

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:SS1 VL R7D
     primer

<400> SEQUENCE: 37
catgattgct ggatcctgag tgagctc    27

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence:SS1 VL A80E
     primer

<400> SEQUENCE: 38
ctggcagtaa tacgtagcat catcttcctc ctccacgctg c    41

<210> SEQ ID NO 39
<211> LENGTH: 64
<212> TYPE: DNA
<213> ORGANISM: Artificial Sequence
<220> FEATURE:
<223> OTHER INFORMATION: Description of Artificial Sequence:SS1 VH
     Q1EK13Q primer

<400> SEQUENCE: 39
aagcgcgcag gctgctcgag ctcaggccca gactgctgca gttgtacctc catatgtata    60
tctc    64

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence:SS1 VH
     S75QS82BNS84N primer

<400> SEQUENCE: 40
tgcagagtct tcattttcaa ttaaccatta catacttttta ctttctac    48

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence:B3 VL L3E
     primer

<400> SEQUENCE: 41
caatggagac tgggtcatct ccacgtccat atgtatatct ccttc    45

<210> SEQ ID NO 42
<211> LENGTH: 51
<212> TYPE: DNA

```
<213> ORGANISM: Artificial Sequence
<220> FEATURE:
<223> OTHER INFORMATION: Description of Artificial Sequence:B3 VL K103D
      primer

<400> SEQUENCE: 42
ctcgggacct ccggaagcat ctatttccag atctgtccca cagccgaacg t          51

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus addition

<400> SEQUENCE: 43

Lys Asp Glu Leu
  1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus addition

<400> SEQUENCE: 44

Arg Glu Asp Leu
  1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 45

Gly Gly Gly Ser
  1

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:amino acid
      positions 1-6 mutated in RFB-4

<400> SEQUENCE: 46

Glu Val Gln Leu Val Glu
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:amino acid
      positions 1-6 mutated in Anti-Tac

<400> SEQUENCE: 47

Gln Val His Leu Gln Gln
  1               5
```

REDUCTION OF THE NONSPECIFIC ANIMAL TOXICITY OF IMMUNOTOXINS BY MUTATING THE FRAMEWORK REGIONS OF THE FV TO LOWER THE ISOELECTRIC POINT

CROSS-REFERENCES TO RELATED APPLICATIONS

This application claims priority from U.S. Provisional Patent Application No. 60/249,805, filed Nov. 17, 2000, the contents of which are incorporated herein by reference.

STATEMENT AS TO RIGHTS TO INVENTIONS MADE UNDER FEDERALLY SPONSORED RESEARCH OR DEVELOPMENT

Not applicable.

BACKGROUND OF THE INVENTION

Recombinant toxins are chimeric proteins in which a cell targeting moiety is fused to a toxin (Pastan et al., *Science*, 254: 1173-1177 (1991)). If the cell targeting moiety is the Fv portion of an antibody, the molecule is termed a recombinant immunotoxin (Chaudhary et al. *Nature*, 339: 394-397 (1989)). The toxin moiety is genetically altered so that it cannot bind to the toxin receptor present on most normal cells. Recombinant immunotoxins selectively kill cells which are recognized by the antigen binding domain. Fv fragments are the smallest functional modules of antibodies. When used to construct immunotoxins, Fv fragments are better therapeutic reagents than whole IgGs because their small size facilitates better tumor penetration (Yokota et al., *Cancer Res.*, 52: 3402-3408 (1992)). Initially, Fvs were stabilized by making recombinant molecules in which the Variable Heavy (VH) and Variable Light (VL) domains are connected by a peptide linker so that the antigen binding domain site is regenerated in a single protein (a single chain Fv, or "scFv") (Bird R., et al., *Science*, 242:423-426 (1988)). Many Fvs, however, could not be stabilized by this approach.

An alternative approach is to stabilize the Fv by a disulfide bond that is engineered between framework regions of the two Fv domains. The disulfide-bond stabilized Fv (termed a "dsFv") is fused to the toxin through either of the Fv domains (Brinkmann et al., *Proc Natl Acad Sci* (USA), 90: 7538-7542 (1993)). One striking difference between scFv immunotoxins and dsFv immunotoxins is that dsFv immunotoxins are more stable. Also, dsFv immunotoxins can often be produced with higher yields than scFv immunotoxins (Reiter et al., *Biochem*, 33: 5451-5459 (1994)).

During the past several years, a number of recombinant toxins have been made using different antibodies ("Abs") (Reiter and Pastan, Trends Biotechnol., 16:513 (1998)). Several of these recombinant immunotoxins have now been evaluated in phase I trials in patients with cancer. All the recombinant immunotoxins that have been brought to clinical trials have been shown to reduce the size of human cancer xenografts growing in nude mice and to be relatively well tolerated by mice and monkeys (Reiter and Pastan, supra). In a phase I trial, eight partial responses were observed in patients with hematopoietic malignancies treated with an immunotoxin, called anti-Tac(Fv)-PE38 (also known as LMB-2), directed against the α subunit of the IL-2 receptor. Side effects have been observed, however, that cannot be attributed to targeting IL-2R positive cells. These side effects limit the amount of immunotoxin that can be given to humans.

The toxic side effects of recombinant immunotoxins are of two types. One type of toxicity results from specific targeting of normal cells which display the same antigen ("Ag") as the cancer cell. The second type of toxicity is nonspecific and usually is characterized by damage to liver cells; this increases the serum levels of serum glutamic oxaloacetic transaminase and serum glutamic pyruvate transaminase (Kreitman and Pastan, Semin. Cancer Biol., 6:297 (1995)), although other toxic effects may occur (Kreitnan and Pastan, Adv. Drug Delivery Rev., 31:53 (1998)).

Some attempts have been made to alter the toxicity of immunoconjugates such as immunotoxins. Morgan, Jr. et al., U.S. Pat. No. 5,322,678, states that the charge of antibodies can be modified to alter their uptake by the kidneys and hence affect their serum half-life. It indicates that antibodies with high positive charges at physiological pH, such as antibodies with highly basic isoelectric points (pI), are likely to undergo charge interaction with negatively charged patches in the glomeruli of the kidney and to be rapidly cleared from the circulation. The patent states that acidic shifts can be are made by reacting antibodies or antibody fragments with succinic anhydride to modify lysine residues.

Kim et al., J. Label. Compd. Radiopharm. XL:422-430 (1997) states that anti-Tac disulfide stabilized immunoconjugates acylated with glycolate to lower their pI had decreased renal uptake without altering tumor uptake.

Kobayashi et al., Cancer Res. 59:422-430 (1999) states that glycolated, unconjugated anti-Tac antibody fragments known as Fabs which were more anionic had less renal clearance and higher tumor accumulation.

SUMMARY OF THE INVENTION

The invention provides recombinant immunotoxins which exhibit reduced liver toxicity compared to their parental immunotoxins. The recombinant immunotoxins comprise an antibody or antigen-binding fragment thereof and a toxin moiety, the toxin moiety of the parental immunotoxin having a pI less than 8, the recombinant immunotoxin comprising an antibody or antigen-binding fragment thereof and an toxin moiety, wherein the antibody or antigen-binding fragment of the recombinant immunotoxin comprises at least one substitution of a negatively charged amino acid for a uncharged or positively charged amino acid on a surface of a framework region of the parental antibody or antigen-binding fragment thereof, and further wherein the recombinant immunotoxin has a pI below about 8.0 resulting from the substitution of amino acids in the antibody or antigen-binding fragment thereof. In some embodiments, the antibody or antigen-binding fragment thereof of said recombinant immunotoxin has a pI, which pI is at least 4 units less than the pI of the parental antibody or antigen-binding fragment thereof.

In one set of preferred embodiments, the parental antibody or antigen-binding fragment thereof is an anti-IL2 receptor antibody or antigen-binding fragment thereof, an anti-mesothelin antibody or antigen-binding fragment thereof, or an anti-LewisY antigen antibody or antigen-binding fragment thereof. In a preferred subset of this set of embodiments, the parental antibody is an anti-Tac antibody or antigen-binding fragment thereof. In some embodiments, the parental antibody or antigen-binding fragment thereof is an M1 dsFv (SEQ ID NOS:2 and 9) or scFv. Further, in some embodiments, the recombinant antibody or antigen-binding fragment thereof has a percent sequence identity that is 90% or more identical to SEQ ID NOS:3 and 10 (the amino acid sequence of M16) and wherein $V_H$ chain positions 13 and 73 are occupied by negatively charged residues, $V_L$ chain positions 18, 45 and 77 are occupied by uncharged residues, and $V_L$ chain positions 103 and 107 are occupied by negatively charged residues, all positions being numbered according to FIG. 2. In some embodiments, these recombinant immunotoxins have an amino acid residue at least one position in a framework region, which position is determined according to FIG. 2, wherein said residue in said position of said framework region is an amino acid residue selected from the group consisting of amino acid residues set forth in a "Percent Frequency" Table of FIG. 2 for said position. In a particularly preferred embodiment, the antibody or antigen-binding fragment thereof has the sequence of SEQ ID NOS:3 and 10 (antibody M16).

In another group of embodiments, the parental antibody or antigen-binding fragment thereof is selected from the group consisting of SS1 and B3. In a subgroup of this group, the parental antibody is SS1 and the recombinant antibody or antigen-binding fragment thereof has a percent sequence identity that is 90% or more identical SEQ ID NOS:5 and 12 (to the amino acid sequence of St6 dsFv), wherein $V_H$ chain position 1 is occupied by a negatively charged residue, and further wherein $V_L$ chain positions 7, 60, 80, and 107 are occupied by negatively charged residues, all positions being numbered according to FIG. 2. In some embodiments, these recombinant immunotoxins have an amino acid residue at least one position in a framework region, which position is determined according to FIG. 2, wherein said residue in said position of said framework region is an amino acid residue selected from the group consisting of amino acid residues set forth in a "Percent Frequency" Table of FIG. 2 for said position. In a particularly preferred embodiment, the antibody or antigen-binding fragment thereof is an St6 dsFv (SEQ ID NOS:5 and 12) or scFv. In a second subgroup, the parental antibody is an anti-B3 antibody and the recombinant antibody or antigen-binding fragment thereof has a sequence identity that is 90% or more identical to SEQ ID NOS:7 and 14 (the amino acid sequence of Mt9 dsFv), wherein VL positions 3, 103, and 107 are occupied by negatively charged residues, all positions being numbered according to FIG. 2. In some embodiments, the recombinant immunotoxin has an amino acid residue at least one position in a framework region, which position is determined according to FIG. 2, wherein said residue in said position of said framework region is an amino acid residue selected from the group consisting of amino acid residues set forth in a "Percent Frequency" Table of FIG. 2 for said position. In a particularly preferred embodiment, the antibody or antigen-binding fragment thereof is Mt9 dsFv (SEQ ID NOS:7 and 14) or scFv.

The recombinant immunotoxins described above preferably have a toxin moiety is selected from the group consisting of Pseudomonas exotoxin A ("PE") or a cytotoxic fragment or mutant thereof, Diphtheria toxin or a cytotoxic fragment or mutant thereof, ricin or a cytotoxic fragment thereof, abrin or a cytotoxic fragment thereof, saporin or a cytotoxic fragment thereof, pokeweed antiviral toxin or a cytotoxic fragment thereof, and bryodin 1 or a cytotoxic fragment thereof. In some preferred embodiments, the toxin moiety is selected from the group consisting of PE38, PE35, PE40, PE4E, and PE38QQR.

The invention further provides compositions comprising any of the above-described recombinant immunotoxins in a pharmaceutically acceptable carrier.

The invention further provides nucleic acid sequences encoding the recombinant immunotoxins described above, as well as expression cassettes comprising a promoter operably linked to a nucleic acid molecule encoding one of these recombinant immunotoxins. The invention further provides host cells comprising one or more of these expression cassettes.

In another set of embodiments, the invention provides methods of killing a malignant cell bearing an antigen, comprising contacting the cell with a recombinant immunotoxin of the invention, as described above, wherein the antibody or antigen-binding fragment of said immunotoxin specifically binds to said antigen. In preferred embodiments, the antigen is selected from the group consisting of an IL-2 receptor, mesothelin, and a Lewis$^Y$ antigen. In some preferred embodiments, the antigen is an IL-2 receptor and the antibody or antigen-binding fragment thereof is an anti-TAC antibody. In some of these embodiments, the antigen is an IL-2 receptor and the anti-TAC antibody or antigen-binding fragment thereof is a M16 dsFv (SEQ ID NO:3 and 10) or scFv. 40. In some preferred embodiments, the antigen is mesothelin and the antibody or antigen-binding fragment thereof is an anti-mesothelin antibody. In some of these embodiments, the anti-mesothelin antibody or antigen-binding fragment thereof is a St6 dsFv (SEQ ID NOS:5 and 12) or scFv. In other preferred embodiments, the antigen is a Lewis$^Y$ antigen and the and the antibody or antigen-binding fragment thereof is an anti-Lewis$^Y$ antibody. In some of these embodiments, the antigen is a Lewis$^Y$ antigen and the anti-Lewis$^Y$ antibody is a Mt9 dsfv (SEQ ID NOS:7 and 14) or scFv.

In another group of embodiments, the invention provides for the use of the recombinant immunotoxins of the invention for the manufacture of a medicament to inhibit the growth of a cancer cell, which cancer cell bears an antigen specifically bound by the antibody or antigen-binding fragment thereof of said immunotoxin. In some of these embodiments, the invention provides a use for the manufacture of a medicament to inhibit the growth of a cancer cell, wherein the parental antibody or antigen-binding fragment thereof is an anti-IL2 receptor antibody or antigen-binding fragment thereof, an anti-mesothelin antibody or antigen-binding fragment thereof, or an anti-LewisY antigen antibody or antigen-binding fragment thereof. In one preferred group of embodiments, the recombinant antibody or antigen-binding fragment thereof has an amino acid sequence that has a percent sequence identity that is 90% or more identical to SEQ ID NOS:3 and 10 (M16), wherein $V_H$ chain positions 13 and 73 are occupied by negatively charged residues, wherein $V_L$ chain positions 18, 45 and 77 are occupied by uncharged residues, and wherein $V_L$ chain positions 103 and 107 are occupied by negatively charged residues, all positions being numbered according to a Percent Frequency table of FIG. 2. In some of these embodiments, the recombinant antibody or antigen binding fragment thereof has amino acid residues at positions in framework regions which positions are determined according to a "Percent Frequency" table of FIG. 2, which antibody has an amino acid sequence selected from the group consisting of SEQ ID NOS:3 and 10 (M16), or a sequence in which residues at positions in framework regions of M16 have been mutated to be amino acid residues selected from the group consisting of residues set forth for that position in a "Percent Frequency" table of FIG. 2.

In particularly preferred embodiments, the antibody or antigen binding fragment thereof is M16 (SEQ ID NOS:3 and 10).

In a further set of preferred embodiments, the invention provides uses of the recombinant immunotoxins of the invention for the manufacture of a medicament to inhibit the growth of a cancer cell, in which the recombinant antibody or antigen-binding fragment thereof of the immunotoxin has an amino acid sequence with a percent sequence identity 90% or more identical to the amino acid sequence of St6 dsFv (SEQ ID NOS:5 and 12), and wherein $V_H$ chain position 1 is occupied by a negatively charged residue and $V_L$ chain positions 7, 60, 80, and 107 are occupied by negatively charged residues, all positions being numbered according to a "Percent Frequency" table of FIG. 2. In some of these embodiments, the recombinant antibody or antigen binding fragment thereof has amino acid residues at positions in framework regions which positions are determined according to a "Percent Frequency" table of FIG. 2, which antibody has an amino acid sequence selected from the group consisting of a sequence identical to that of St6 (SEQ ID NOS:5 and 12), or a sequence in which residues at positions in framework regions of St6 have been mutated to be amino acid residues selected from the group consisting of residues set forth for that position in a "Percent Frequency" section of FIG. 2. In a particularly preferred embodiment, the antibody or antigen binding fragment thereof is St6 (SEQ ID NOS:5 and 12).

In another set of embodiments, the invention provides uses of the recombinant immunotoxins of the invention for the manufacture of a medicament to inhibit the growth of a cancer cell, in which the recombinant antibody or antigen-binding fragment thereof of the immunotoxin has an amino acid sequence with a percent sequence identity that is 90% or more identical to the amino acid sequence of SEQ ID NOS:7 and 14 (Mt9 dsFv) and wherein $V_L$ chain positions 3, 103 and 107 are occupied by negatively charged residues, all positions being numbered according to a "Percent Frequency" table of FIG. 2. In some of these embodiments, the recombinant antibody or antigen binding fragment thereof has amino acid residues at positions in framework regions which positions are determined according to a numbering system of a "Percent Frequency" table of FIG. 2, which antibody has an amino acid sequence selected from the group consisting of a sequence identical to that of Mt9 (SEQ ID NOS:7 and 14), or a sequence in which residues at positions in framework regions of Mt9 have been mutated to be amino acid residues selected from the group consisting of residues set forth for that position in the "Percent Frequency" table of FIG. 2. In a particularly preferred embodiment, the antibody or antigen binding fragment thereof is Mt9 (SEQ ID NOS:7 and 14).

M16=Fv portion of anti-Tac antibody in which neutral and basic residues are mutated to acidic residues ($V_L$ sequence: SEQ ID NO:3; $V_H$ sequence: SEQ ID NO:10); SS1=Fv portion of an anti-mesothelin antibody ($V_L$ sequence: SEQ ID NO:4; $V_H$ sequence: SEQ ID NO:11); ST6=Fv portion of antibody SS1 in which neutral and basic residues have been mutated to acidic residues ($V_L$ sequence: SEQ ID NO:5; $V_H$ sequence: SEQ ID NO:12); dsB3=disulfide stabilized B3 Fv ($V_L$ sequence: SEQ ID NO:6; $V_H$ sequence: SEQ ID NO:13); "Mt9"=Fv portion of antibody B3 in which neutral and basic residues have been mutated to acidic residues ($V_L$ sequence: SEQ ID NO:7; $V_H$ sequence: SEQ ID NO:14). Vertical shaded areas identify positions at which residues were mutated from that of the amino acid of the parental antibody. All amino acids are designated by standard single letter code. The lower portion of each panel, labeled "Percent Frequency," is a table of amino acids sorted into bands denoting, for each position of the Kabat sequence, the percentage of antibodies in the Kabat database in which the amino acids appears at that position of the framework regions of the VL and VH chains, respectively. For example, in the top panel, reading vertically down from Kabat position 1, the amino acid "D" (aspartic acid) occurs in from 50-100% of all antibodies, "Q" (glutamine) occurs in 10-20% of all antibodies, "E" (glutamic acid) occurs in 5-10% of all antibodies, and "N" (asparagine) occurs in only 2-3% of antibodies. Dashes (--) in the lines corresponding to the individual Fvs, refers to the absence of residues present in the Kabat numbering sequence. CDRs are regions that vary among antibodies since the CDRs determine binding specificity. The dashes in the 50-100% line for the CDRs denote that no frequency determination was made for residues in the CDRs.

Figure 3:
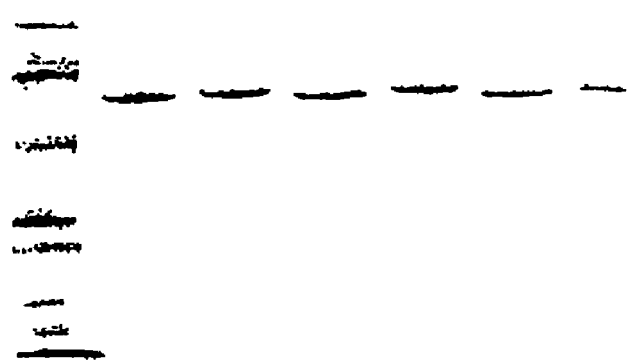
Figure 3:
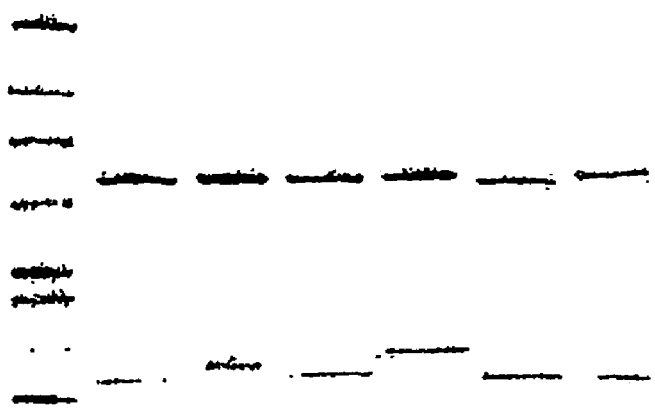

FIG. 3. Polyacrylamide gel electrophoresis of purified recombinant immunotoxins. The purified proteins were run on 4-20% gradient SDS-polyacrylamide electrophoresis gels under non-reducing conditions (A), and under reducing conditions (B). The gels were stained with Coomasie Blue. Lane 1, M1(dsFv)-PE38; lane 2, M16(dsFv)-PE38; lane 3, SS1 (dsFv)-PE38; lane 4, St6(dsFv)-PE38; lane 5, B3(dsFv)-PE38; lane 6, Mt9(dsFv)-PE38; M, molecular mass standards are (top to bottom) 204, 120, 80, 50, 34, 29, 21.6 and 7 kDa, respectively.

Figure 4:
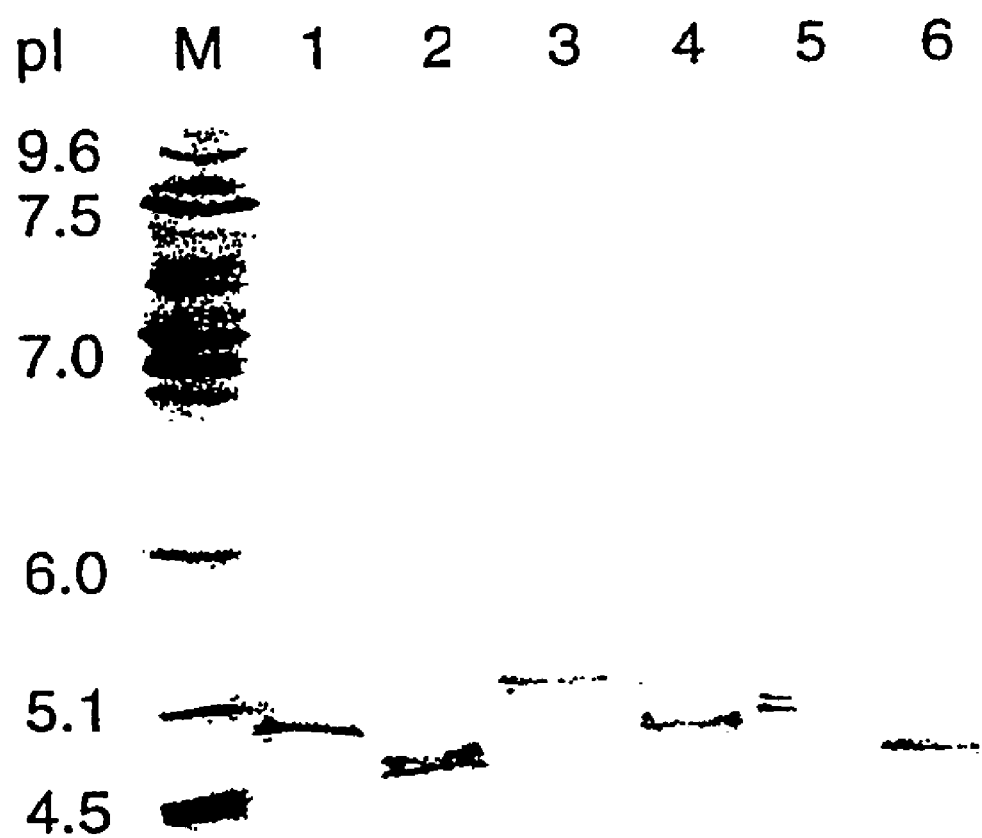

FIG. 4. Isoelectric focusing of immunotoxins. M, pI standard marker; lane 1, M1(dsFv)-PE38; lane 2, M16(dsFv)-PE38; lane 3, SS1(dsFv)-PE38; lane 4, St6dsFv)-PE38; lane 5, B3(dsFv)-PE38; lane 6, Mt9(dsFv)-PE38, respectively.

Figure 5:
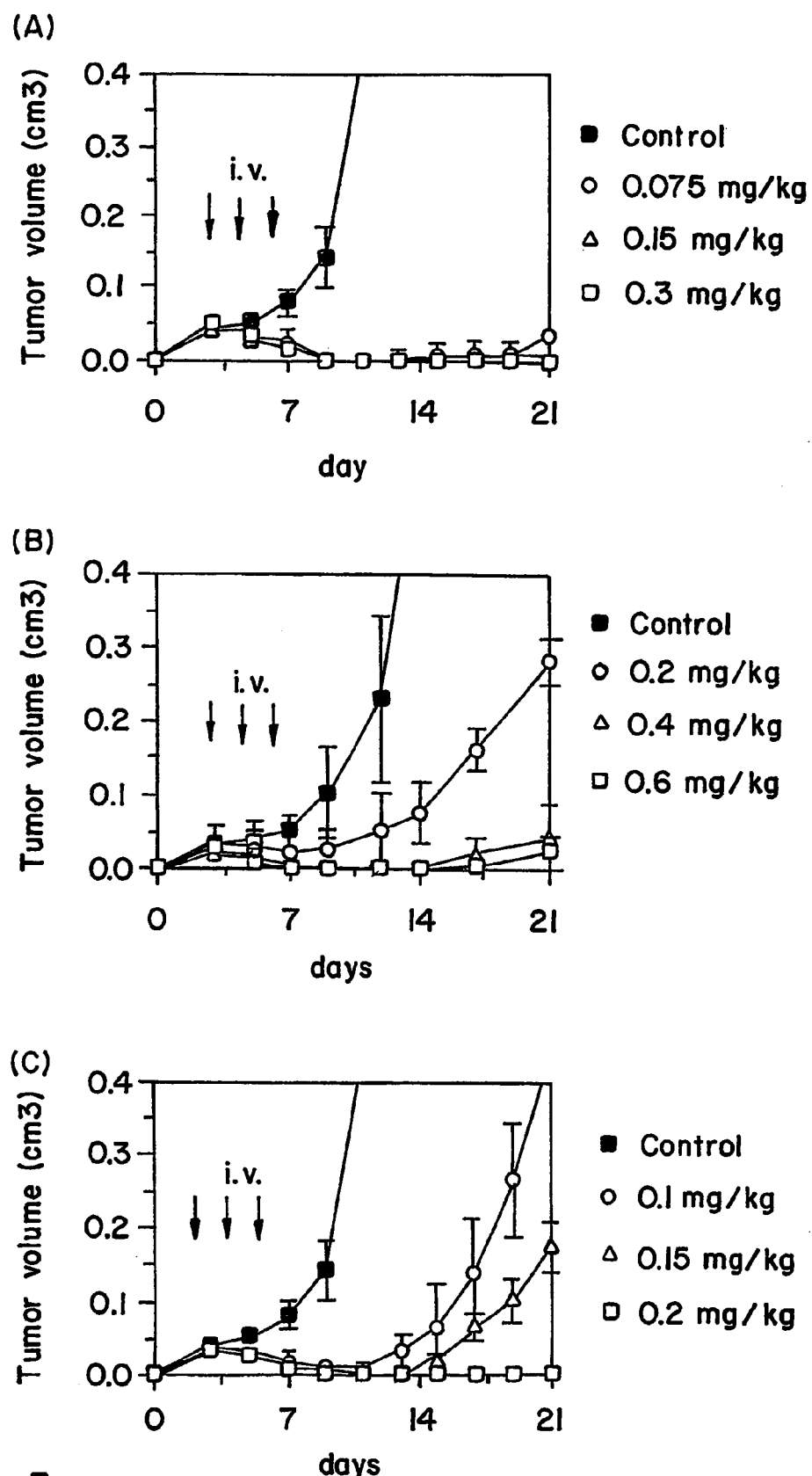

FIG. 5. Antitumor activities of M16(dsFv)-PE38 (shown in panel A), St6(dsFv)-PE38 (panel B), and Mt9(dsFv)-PE38 (panel C) in nude mice bearing human cancer cells which have antigen expression (ATAC4 cells in panel A, A431-K5 cells in panel B, and A431 cells in panel C). Groups of five animals were injected subcutaneously with $3 \times 10^6$ human cancer cells on day 0. Tumors approximately 0.05 cm$^3$ in size developed in animals by day 4 after tumor implantation. Starting on day 4, animals were treated with intravenous injections of one of the immunotoxins, diluted in 0.2 ml of PBS/0.2% HAS, or of carrier alone, as a control. Animals administered immunotoxins were divided into three cohorts; each cohort received a different dosage of the immunotoxin. The particular dosages administered of each immunotoxin are set forth in the legend to the right of each panel. Therapy was given once every other day (on day 4, 6, and 8, Arrow head). No death or toxicity was observed at these doses.

Figure 6:
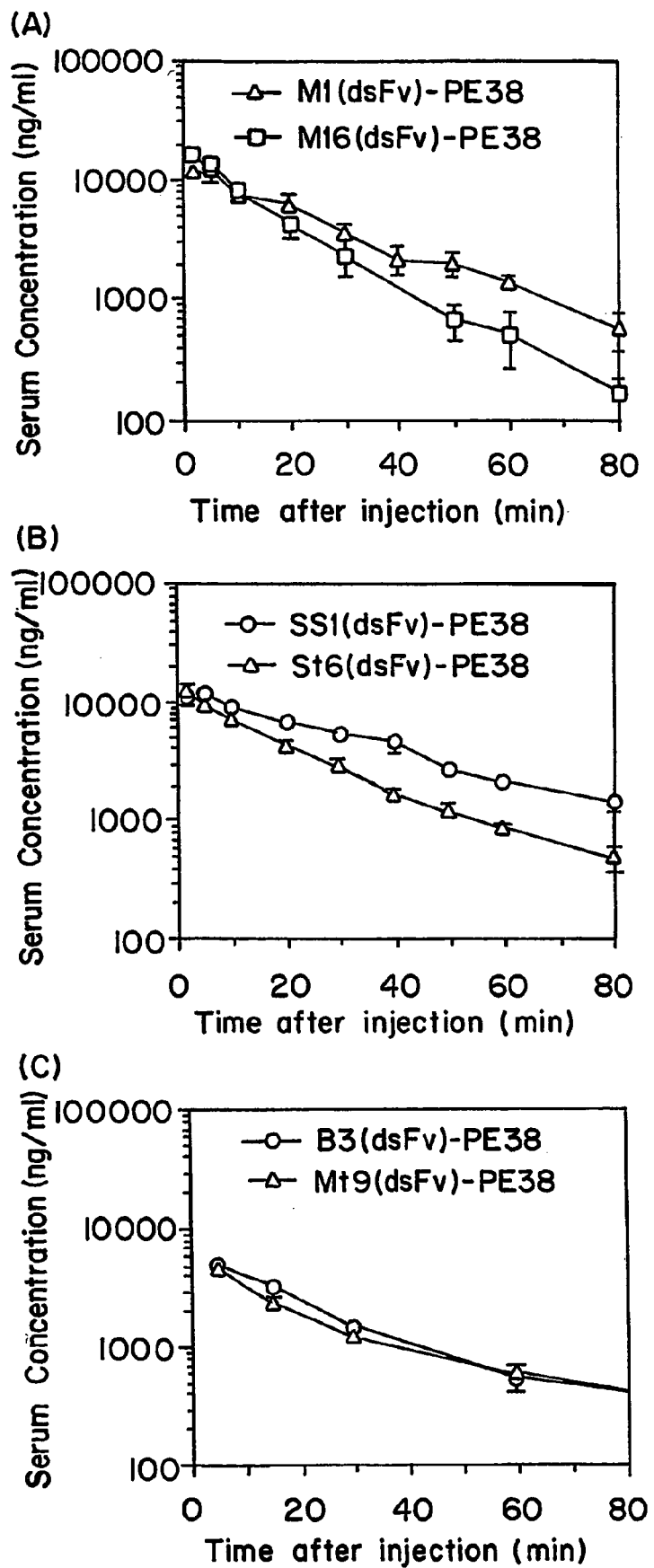

FIG. 6. Pharmacokinetics of M1(dsFv)-PE38 and M16 (dsFv)-PE38 (shown in panel A), SS1(dsFv)-PE38 and St6 (dsFv)-PE38 (panel B), and B3(dsFv)-PE38 and Mt9(dsFv)-PE38 (panel C) in mice. NIH Swiss mice were injected intravenously with 5 μg of M1(dsFv)-PE38, M16(dsFv)-PE38, SS1(dsFv)-PE38, or St6(dsFv)-PE38, or 10 μg of B3(dsFv)-PE38 or Mt9(dsFv)-PE38. Blood samples were drawn at different times. The level of immunotoxin in blood was measured by a bioassay in which serum samples were incubated with human cancer antigen positive cells (ATAC4 cells for A, A431-K5 cells for B, or A431 cells for C), and the ability of the serum sample to inhibit protein synthesis was measured. Results are the average of 4 or 5 animals for each time point±SE.

Figure 7:
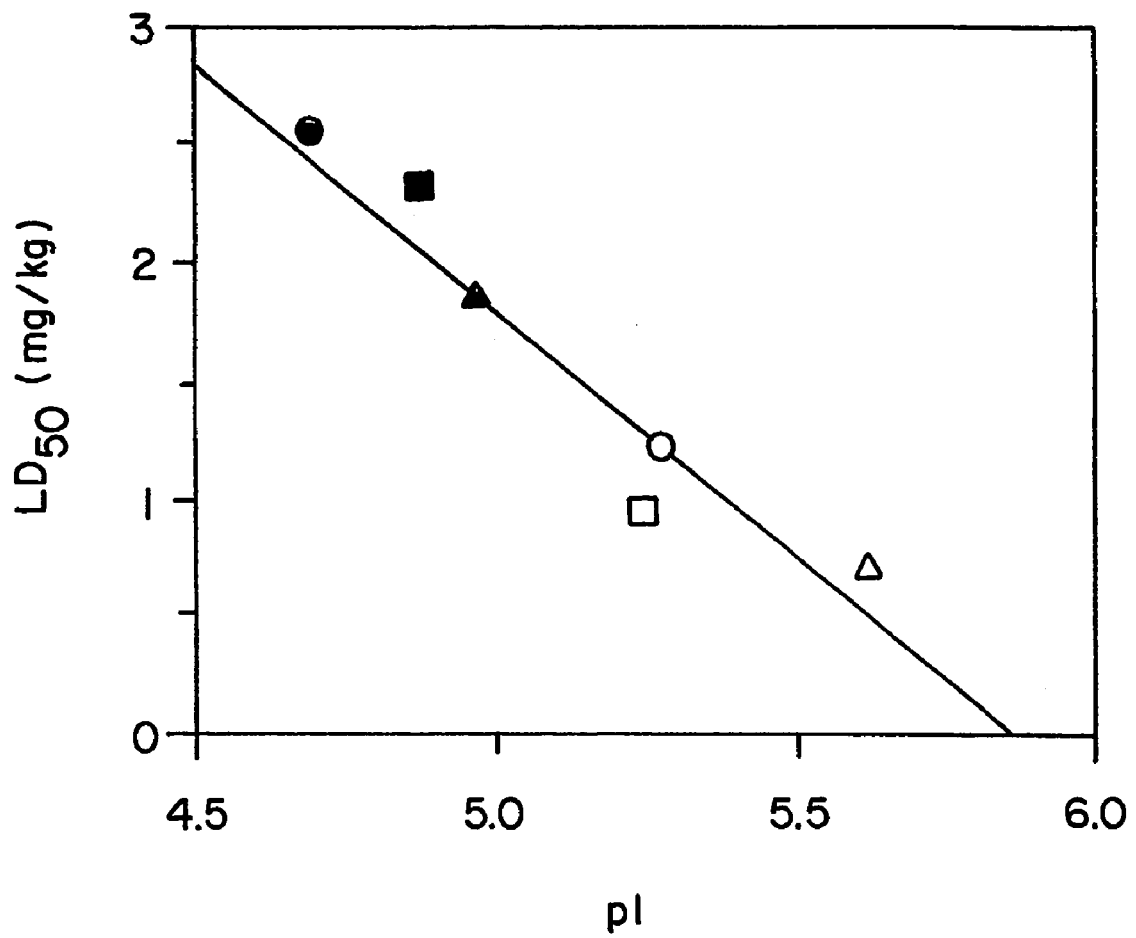

FIG. 7. Correlation between pI and mice toxicity ($LD_{50}$).

---

Symbols indicate the following:

○ M1(dsFv)-PE38,   ● M16(dsFv)-PE38,   △ SS1(dsFv)-PE38,
▲ St6(dsFv)-PE38,   □ B3(dsFv)-PE38,   ■ Mt9(dsFv)-PE38 n = 6, r = −0.9691, p = 0.0014.

---

DETAILED DESCRIPTION

Introduction

It has now been discovered that the nonspecific toxicity of immunotoxins which use antibodies or fragments thereof as targeting moieties can be reduced by mutating specific residues of the Fv of the antibody to reduce the isoelectric point ("pI") of the Fv portion of the immunotoxin, without affecting the toxicity of the immunotoxin to the targeted cells or other desirable characteristics. Moreover, a method has been developed which permits the rational selection of residues of an antibody to be mutated, permitting the predictable development of immunotoxins which will retain the selective cytotoxicity and stability of the starting immunotoxin, but which have lower toxicity than the starting immunotoxin. Surprisingly, the pI of the Fv portion of the immunotoxin can be reduced by more than four units when the reduction is performed according to the methods taught herein. Since animal toxicity is a limiting factor in administering immunotoxin therapeutically, the immunotoxins of the invention, which have lower toxicity, can be administered in higher doses than current immunotoxins. The higher doses, in turn, facilitate the killing of a higher percentage of the target cells, and an improved therapeutic outcome.

The Fv regions of the immunotoxin are mutated in a manner which succeeds in decreasing the pI without causing a substantial decrease either in the targeting capability of the immunotoxin or the toxic effect of the immunotoxin on the targeted cells. Conversely, it is generally not necessary to make changes to the toxic moiety of the immunotoxin to reduce pI. Modifications to the toxic moiety may, however, be made to reduce undesirable characteristics, such as non-specific binding of the toxin, or to enhance desirable characteristics, such as internalization of the toxin into a target cell or the translocation of the toxin into the cytosol of the cell. Such modifications are known in the art and are discussed further below.

Any immunotoxin of interest can predictably have its nonspecific toxicity reduced by rationally mutating specific residues chosen according to the following protocol, without interfering antigen binding, stability, or normal antibody folding. The protocol achieves this goal, in part, by homing in on particular candidate residues, and by determining whether the candidate residue can be mutated by comparing that residue to the ones most commonly found at the same position in hundreds, if not thousands, of other antibodies. In essence, the method uses natural evolution as a guide to whether mutation of the candidate residue will be advantageous or contraindicated by looking at thousands of antibodies to determine if a negative charge can be placed at particular positions in the structure of the antibody. If evolution has indicated a negative charge can be placed at the position of the candidate residue, than the method permits mutation of the residue to one containing a negative charge. If the candidate residue is at a position where a negatively charged is never found, it is considered likely that a negative charge at that position is disadvantageous, and a mutation is not made.

The protocol identifies residues that are candidates for mutation as follows. First, the heavy and light chains of the Fv region of the antibody of interest are aligned with the Kabat numbering system for amino acid residues in the $V_H$ and $V_L$ chains. (Kabat, E., et al., SEQUENCES OF PROTEINS OF IMMUNOLOGICAL INTEREST, U.S. Department of Health and Human Services, ($5^{th}$ Ed., 1991)) (hereafter, "Kabat"). The Kabat numbering system is the most widely used system in the art for numbering residues of antibody chains consistently so that one of skill can determine, for example, which residues are within complementarity determining regions ("CDRs") and which are within framework regions, and persons of skill in the art are well familiar with determining Kabat positions for antibody chains. The Kabat database is now too large to be maintained in print and is available online at http://immuno.bme.nwu.edu/. if the amino acid sequences of the antibody chains are not known, the sequence should first be determined to permit the alignment to be made. Conveniently, this can be done by cloning the gene and determining the amino acid sequence encoded by the nucleic acid sequence. Alternatively, the sequence of the amino acids of the antibody can be determined chemically.

Figure 2A:
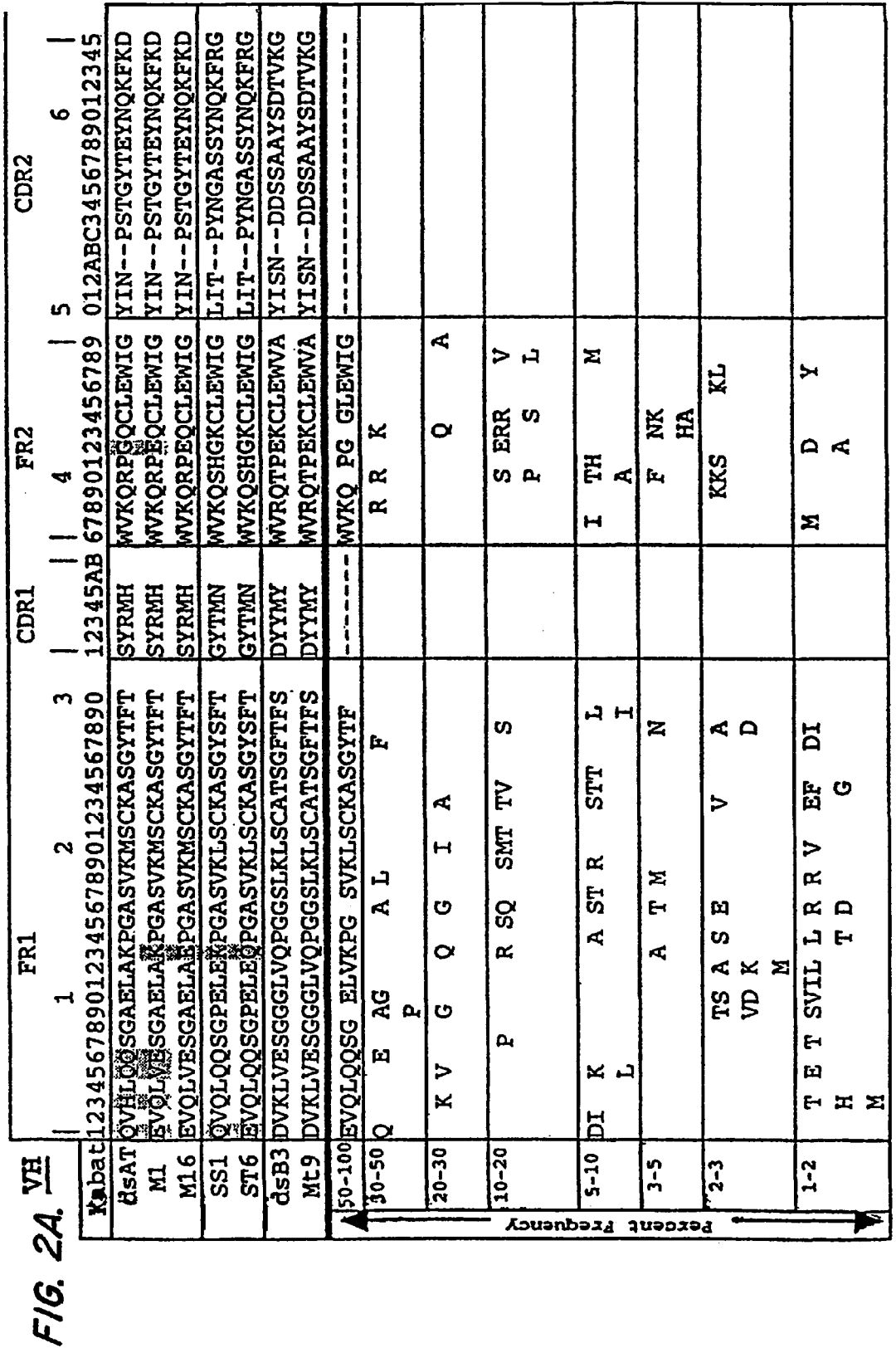
FIG. 2. Sequences of Fvs aligned with frequency table. Legend: VL denotes amino acid sequence of variable light chain; VH denotes amino acid sequence of variable heavy chain. "Kabat" denotes amino acid residue number numbered by system as set forth in Kabat et al. (1987). "FR"=framework region; "CDR"=complementarity determining region. "dsAT"=disulfide stabilized anti-Tac Fv ($V_L$ sequence: SEQ ID NO:1; $V_H$ sequence: SEQ ID NO:8); M1=Fv portion of anti-Tac antibody in which selected neutral residues are mutated to acidic residues ($V_L$ sequence: SEQ ID NO:2; $V_H$ sequence: SEQ ID NO:9)

FIG. 2 shows an alignment with the Kabat numbering of the amino acid sequences of the light and the heavy chains of six exemplary Fvs: a disulfide stabilized anti-Tac Fv (denoted as "dsAT") (the amino acid sequence of the $V_L$ chain ("$V_L$ sequence") is SEQ ID NO:1; the amino acid sequence of the $V_H$ chain ("$V_H$ sequence") is SEQ ID NO:8), a mutant of dsAT in which certain neutral residues of the CDRs were mutated to acidic residues ("M1") ($V_L$ sequence: SEQ ID NO:2; $V_H$ sequence: SEQ ID NO:9), a mutant of $M_1$ in which certain neutral and basic residues of the CDRs were mutated to acidic residues ("M16") ($V_L$ sequence: SEQ ID NO:3; $V_H$ sequence: SEQ ID NO:10), an anti-mesothelin Fv known as SS1 ($V_L$ sequence: SEQ ID NO:4; $V_H$ sequence: SEQ ID NO:11), a mutant of SS1 in which certain neutral and basic residues of the CDRs were mutated to acidic residues ("ST6") ($V_L$ sequence: SEQ ID NO:5; $V_H$ sequence: SEQ ID NO:12), a disulfide stabilized anti-LewisY antigen Fv ("dsB3") ($V_L$ sequence: SEQ ID NO:6; $V_H$ sequence: SEQ ID NO:13), and a mutant of dsB3 in which certain neutral and basic residues of the CDRs were mutated to acidic residues ("Mt9") ($V_L$ sequence: SEQ ID NO:7; $V_H$ sequence: SEQ ID NO:14).

Second, the frequency in which particular residues are found at each location in the framework regions of Fvs are noted. This information is presented in tabular form in FIG. 2, and presents an analysis of the current Kabat database of the residues found at each position of thousands of antibodies of all classes, as set forth in the Kabat database website, http://immuno.bme.nwu.edu. The top panel of FIG. 2 presents this information for positions of the variable light ("$V_L$" or "VL") chain of the Fv, while the bottom panel of the Figure presents this information for positions of the variable heavy ("$V_H$") chain. The frequency with which a particular residue is found at a particular position in the framework region of the Fv is set forth in the portion of the panel marked on the left side as "Percent Frequency," which is sometimes referred to herein as the Percent Frequency Table. The part of the panel denoted by the arrows is broken into percentage bands showing the percent of antibodies in which a particular residue appears at the particular position.

The Table is read vertically, starting from the Kabat position number at the top of the panel, and may be most easily understood with reference to an example. Turning to the top panel, which describing the $V_L$ portion of the Fv, the line setting forth the Kabat position numbers is read horizontally until the residue of interest is reached. In this example, it will be assumed the first residue of interest is found at Kabat position 1, which appears just to the right of the word "Kabat." Proceeding down vertically, the residue which appears at that position in the $V_L$ of the dsAT Fv is "Q", the standard single letter code for glutamine; the $V_L$s of the other five Fvs listed have the residue "D" (aspartic acid) at position 1. Proceeding down into the "Percent Frequency" Table below the aligned Fv regions, the reader finds that 50-100% of all antibodies have a "D" (aspartic acid) at position 1, that 10-20% of all antibodies have a "Q" (glutamine) at that position, that 5-10% of all antibodies have an "E" (glutamic acid) at position 1, and that 2-3% of antibodies have a and "N" (asparagine) at position 1. It therefore appears that, if desired, position 1 can be mutated to a "D," "Q," "E," or "N" without affecting the ability of the Fv to function, while other residues at that position would probably not be desirable. In contrast, position 23 of the light chain is always occupied by a "C" (cysteine) residue, as can be seen by the fact that a "C" appears in the "50-100%" band, while no other residue appears in any other percentage frequency bands. Similarly, position 88 of the $V_L$ is also always a cysteine. Since positions 23 and 88 of the VL are occupied by a cysteine residue in every antibody in the Kabat database, it is very likely that a cysteine at this position is required for correct function of the Fv. Thus, the Percentage Frequency table set forth in FIG. 2 can be used to determine which residues can be considered permissible substitutions at any given position, and which residues should be considered invariant.

Returning to the protocol, the third step is to identify residues in the alignment which are in a complementarity determining region ("CDR"). CDRs are considered to be involved in antigen recognition and binding. Residues in the CDRs are therefore likely to affect antigen recognition and are excluded from consideration as candidates for mutation. This exclusion is symbolized on the "Percentage Frequency" table in FIG. 2 by a dash (-) in the 50-100% band in each position representing a residue in a CDR (to assist in interpreting the Figure, it is noted that the alignments for the individual Fvs also contain dashes at some positions in the CDRs. A dash in the alignment of any particular the Fvs represents a position in the Kabat numbering system for which there is not a corresponding residue in the Fv when the Fv is aligned. Most commonly, one or more of the CDRs of the particular Fv is shorter than the maximum length permitted for CDRs in the Kabat database. For example, the $V_L$ of Fv dsAT does not have a residue corresponding to positions 27A-28 of the Kabat sequence, while the $V_L$ of Fv Mt9 lacks a residue corresponding to Kabat position 27E.).

Fourth, acidic residues in the Fv are excluded as candidates for mutation, since they are already negatively charged. Fifth, residues which show 100% conservation in the Kabat Percent Frequency table of FIG. 2 are excluded since they are likely to be important to antibody folding or to contribute to other functional characteristics of the molecule. Sixth, positively charged residues which are at positions in the Kabat sequence at which neutral or negative residues never occur on the "Percent Frequency" Table are excluded, in part because that implies that evolution has determined that a positive charge at that position is likely to be advantageous. Similarly, neutral residues which are at positions at which an acidic residue never appears on the Percentage Frequency Table are excluded from consideration as candidates for mutation.

The seventh and eighth factors are based on creating a model of the Fv structure based on the crystal structure of the antibody, if one is available, or of other antibodies in the Kabat class or family in which the Fv of interest is categorized. Many crystal structures of antibodies are now known. As is well known in the art, a model of the crystal structure of the antibody of interest, or an antibody of the same Kabat class, and the position of the candidate residue when aligned with the Kabat numbering system, permits the determination of whether the residue in question is exposed at the surface of the Fv and whether the residue is predicted to interact with other residues in the Fv (for example, by forming hydrogen bonds).

Determinations of whether a particular residue is likely to be exposed at the surface of the Fv and of whether the residue is predicted to interact with other residues in the Fv (by, for example, forming hydrogen bonds), can be performed by building a model structure of the antibody of interest from the sequence alignment to an antibody of the same Kabat class whose structure is known and inspecting the model structure. Modeling from known structures is taught by, e.g., Eigenbrot et al., J. Mol. Biol., 229:969 (1993) and Barry et al., J. Biol. Chem., 269:3623 (1994). Detailed information on modeling antibodies is available at http://antibody.bath.ac.uk. This website is styled "Web Antibody Modeling," or "WAM," and provides software for aligning residues as well as WAM modeling software based on the modeling algorithm "AbM" developed by Martin et al., Meth Enzymol. 203:121 (1991), Martin et al., Proc Natl Acad Sci USA 86:9268 (1989).

Candidate residues which have less than 30% of their surface area exposed are excluded from mutation, since the limited amount of exposure would effectively reduce amount of effect mutating the residue would have on reducing the pI. Residues which are predicted from the crystal structure or by modeling to interact with others are excluded from mutation since it is assumed that a change in charge would change the interaction and consequent function of the Fv. Ninth, the C-terminal residue is considered never to be involved in interactions with other residues, folding, or antigen binding and is always considered a candidate for mutation. This freedom to mutate can be considered to extend to the C-terminal residue and as many as the next four residues most proximal to the C-terminus.

The residues remaining after these exclusions are candidates for mutation. If the residue is basic, it can be replaced with either an acidic or a neutral residue. Guidance as to whether to substitute an acidic or a neutral residue for the basic residue is provided by the Percent Frequency table. If the most common residue found at the position under consideration is neutral, then the first choice for mutation of the existing residue is to substitute a neutral residue at that position. If the most common residue at the position is acidic, then the residue used to replace the existing residue should be acidic. As to the particular neutral or acidic residue to substitute, it is preferable to use the residue most commonly found at that position. Similarly, if the residue which is a candidate for mutation is neutral, an acidic residue can be substituted. Generally, one refers to the Percent Frequency table appearing on FIG. 2 and replaces the candidate residue with the most common acidic residue appearing at the position occupied by the candidate residue.

The value of following some or all of this protocol can be seen by the exemplary studies reported in the Examples. To ensure that the results of the studies have relevance to treatment of humans, the immunotoxins chosen as the parental immunotoxins to be improved are ones that are already showing positive results in human clinical trials. Since immunotoxins which are in clinical trials first underwent extensive pre-clinical animal testing, the positive results achieved in the human clinical trials to date show that the positive results in the pre-clinical animal testing are indeed correlated with like results in humans. Further, to reduce variables irrelevant to larger purposes of the study, all of the immunotoxins used as a toxic moiety a *Pseudomonas* exotoxin A (PE) mutated to remove non-specific binding but to retain cytotoxic capability when directed into cells by a targeting moiety of an immunotoxin. The particular mutant PE used has a molecular weight of 38 kD, and is known as PE38. (Hwang et al., *Cell*, 48: 129-136 (1987)). Other toxic moieties suitable for use in humans as part of recombinant immunotoxins can, however, be used with like results.

As previously noted, six Fvs are set forth on FIG. 2. The first Fv listed is dsAT, used to construct anti-Tac(dsFv)-PE38, which targets the α chain of the IL-2 receptor and which is directed at CD25-expressing hematologic malignancies. dsAT is an anti-Tac Fv which was used as the starting, or "parental" antibody for studies of mutations to reduce pI and, it was hoped, non-specific toxicity. One of the dose limiting toxicities of recombinant immunotoxins is liver damage due to cytokine release. Liver damage due to TNFα release is also a dose limiting toxicity in mice given anti-Tac(scFv)-PE38, the scFv version of the anti-Tac immunotoxin also known as LMB-2. Molecular modeling and site directed mutagenesis was used to lower the pI of the Fv of anti-Tac without decreasing its binding activity. In studies conducted before development of all the steps of the protocol set forth above, the mutations were restricted to mutating neutral residues to acidic amino acids. The resulting Fv was termed "M1." An immunotoxin was constructed containing this mutated Fv, and was termed M1(scFv)-PE38. The toxicity in mice of M1(scFv)-PE38 is more than 3-fold lower than that of anti-Tac(scFv)-PE38. The pI of the Fv of anti-Tac Fv is 10.21. This was lowered to 6.82 in M1 scFv, yet its ability to kill CD25 positive target cells when used in an immunotoxin with the same toxic moiety (PE38) was undiminished. See, Examples 1-3, below.

Other immunotoxins employed in the exemplary studies were: SS1(dsFv)-PE38, an immunotoxin targeted at ovarian cancers and other epithelial cancers expressing the protein mesothelin (Chowdhury et al., *Proc Natl Acad Sci* (USA, 95: 669-674 (1998); Chowdhury et al., *Nature Biotechnol*, 17: 568-572 (1999)), B3(dsFv)-PE38 (LMB9), an immunotoxin targeted at epithelial cancers that express Lewis[Y] (Pastan et al., *Cancer Research*, 51: 3781-3787(1991)), and RFB4 (dsFv)-PE38(BL-22), which is directed at CD22-expressing hematologic malignancies, and which is very well tolerated in mice. Anti-Tac(scFv)-PE38 and RFB4(dsFv)-PE38 have both shown good antitumor activity in patients (Kreitman et al., *Blood*, 94: 3340-334 (1999); Kreitman et al., *J. Clinical Oncology*, 18: 1622-1636 (2000); Kreitman et al., *Clinical Cancer Research*, 6: 1476-1487 (2000)).

As the protocol was developed for mutating antibodies to reduce pI, the initial studies were extended by mutating basic residues to acidic residues. Further, the Fv portion of an immunotoxin was stabilized by replacing the peptide linking the $V_H$ and $V_L$ chains with a disulfide bond introduced into the framework region. Therefore, M1(scFv)-PE38 was first converted into M1(dsFv)-PE38, and then selected basic residues were mutated to acidic residues to form a further mutant, termed M16(dsFv)-PE38. Conversion of scFvs to dsFvs can be performed by published techniques, such as that set forth in Brinkmann et al., Proc Natl Acad Sci (USA) 90:7538-7542 (1993). Similarly, B3(dsFv)-PE38 was mutated by the protocol set forth above to form a mutant known as Mt9(dsFv)-PE38, and SS1(dsFv)-PE38 was mutated to form a mutant known as St6(dsFv)-PE-38. The sequences of the parental and mutated antibodies (SEQ ID NOS:1-14) are set forth in FIG. 2.

The results show that animal toxicity is markedly diminished by lowering the pI of the Fv, while the full antitumor activity of the parental immunotoxin is retained. Further, each of the mutants was as stable at physiological temperature as its parental immunotoxin. Interestingly, in in vivo studies, the pharmacokinetics of the immunotoxins showed that each of the immunotoxins engineered to have a lower pI than that of its parental immunotoxin also had a shorter half-life in the serum than that of its parent in an animal model. See, Example 6, infra. But, the studies also showed that the lower pI mutated immunotoxins had tumor-reducing effects as great as that of the parental immunotoxin. Without wishing to be bound by theory, it is possible that the lower pI of the Fv facilitates specific recognition of the target antigen or enhances cell uptake of the immunotoxin. Thus, while a shorter half-life might normally be correlated with a reduced effect of the immunotoxin, immunotoxins mutated by the methods of the invention surprisingly retain the full activity of the parental immunotoxin against targeted cells.

The results obtained for these three different immunotoxins indicate that the protocol set forth above can be used to reduce the non-specific toxicity of any antibody, or fragment thereof which retains antigen-binding capability, which has not already been the subject of pI-reducing alterations. In general, any Fv can be modified by the procedures set forth above to improve its utility as the targeting portion of an immunotoxin.

In general, disulfide-stabilized Fvs (dsFvs) are more useful in clinical use, and in preferred embodiments, the targeting moiety of the immunotoxin is a dsFv. scFvs can, however, be employed if desired and can be modified to reduce pI and toxicity in the manner set forth above.

In the most preferred embodiments, the $V_L$ and the $V_H$ of the Fv portion of immunotoxins mutated by the methods taught herein have the amino acid sequence of the $V_L$ and $V_H$ chains of M16 (SEQ ID NOS: 3 and 10), of St6 (SEQ ID NOS: 5 and 12), of Mt9 (SEQ ID NOS:7 and 14), or of M1 (SEQ ID NOS:2 and 9). In other preferred embodiments, the $V_L$ and $V_H$ chains of the Fv have about 90% or greater sequence identity amino acid sequences of the $V_L$ and the $V_H$, respectively, M16, St6, Mt9, or M1 (but, of course, do not have the sequence of the parental immunotoxin), and have reduced toxicity compared to the parental immunotoxin. It is desirable that the $V_L$ and the $V_H$ chains of the antibodies or antigen binding fragments thereof retain the pI-lowering mutations of the residues made according to the protocol set forth above. That is, if the protocol indicates that a positively charged residue can be mutated to a negatively charged residue, it is desirable that that mutation be retained in any variation of the sequence. Similarly, if the protocol indicates that a positively charged residue can be mutated to a residue with neutral charge, it is desirable that that mutation also be retained in any variation of the amino acid sequence.

It should be noted that the Percent Frequency Table of FIG. 2 shows which residues vary in thousands of antibodies, and what substitutions occur at various Kabat positions. Thus, while it is generally desirable to retain the mutations of the antibodies to reduce their pI, if desired residues at other positions in the antibody varied by substituting residues according to the Percent Frequency Table of FIG. 2 for the variable light chain or for the variable heavy chain, respectively.

In preferred embodiments, the $V_L$ and $V_H$ of the Fv of the immunotoxins have 91%, 92%, 93%, 94%, 95%, or greater sequence identity to the $V_L$ and $V_H$, respectively, of M16, St6, Mt9, or M1, respectively. The immunotoxins preferably retain at least 75% of the cytotoxicity to targeted cells of the parental immunotoxin, and more preferably 80%, 85%, 90%, 95% or even more of the cytotoxicity of the parental immunotoxin to cells bearing an antigen to which the antibody or antigen-binding fragment thereof specifically binds.

The liver enzyme alanine aminotransferase (ALT), formerly known as sGPT, is considered an indicator of liver inflammation. ALT levels are routinely measured in patients, for example, to monitor the course of chronic hepatitis and of treatments such as the administration of prednisone. ALT levels can conveniently be used as a marker for the overall toxicity of an immunotoxin in animal models by determining whether the level of in the serum is increased by more than 5, 6, 7, 8, 9, 10, or more times 24 hours after administration of an immunotoxin, compared to the level of the liver enzyme in the serum at 3 hours after administration. Immunotoxins which induce a lower level of the enzyme or enzymes at 24 hours are considered to have lower toxicity than immunotoxins which induce higher levels of such enzymes. Conveniently, the toxicity is determined using a mouse model. In preferred embodiments, the immunotoxin does not cause the upper level of the enzyme (even taking into account the error limits of the measure) in the serum of the mice to which it is administered to exceed 220 U/L. In more preferred embodiments, the immunotoxin does not cause the upper level in the serum of the mice to exceed 210 U/L. In even more preferred embodiments, it does not cause the upper level of the serum level to exceed 200 U/L, and in the most preferred embodiments, does not cause it to exceed 190 U/L. A number of devices which analyze ALT levels are commercially available, such as the Boehringer Mannheim ("BM")/Hitachi 917 analyzer (Hitachi Instruments, Inc.), sold by Roche Diagnostics GmbH (Mannheim, Germany).

As noted above, mice are an art-recognized model for testing immunotoxins for their effect on human tumors, and the immunotoxins used as the parental immunotoxins in the exemplary studies herein are already in human clinical trials. Given the lower toxicity to mice shown by the immunotoxins comprising the Fvs mutated by the procedures set forth above, immunotoxins mutated according to the procedures taught herein will exhibit lower toxicity in humans compared to their parental immunotoxins, permitting higher doses to be employed. The higher doses that can be used result in even better killing of tumor cells targeted by these and other immunotoxins mutated according to the invention.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

"Antibody" refers to a polypeptide ligand comprising at least a light chain or heavy chain immunoglobulin variable region which specifically recognizes and binds an epitope (e.g., an antigen). This includes intact immunoglobulins and the variants and portions of them well known in the art such as, Fab' fragments, $F(ab)'_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, Pierce Catalog and Handbook, 1994-1995 (Pierce Chemical Co., Rockford, Ill.); Kuby, J., *Immunology*, $3^{rd}$ Ed., W. H. Freeman & Co., New York (1997).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined (see, Kabat, E., et al., SEQUENCES OF PROTEINS OF IMMUNOLOGICAL INTEREST, U.S. Department of Health and Human Services, (1991), which is hereby incorporated by reference. The Kabat database is now maintained online at http://immuno.bme.nwu.edu/.). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including that of an Fv, scFv, dsFv or Fab. References to "$V_L$" or a "VL" refer to the variable region of an immunoglobulin light chain, including that of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but which have a lower pI.

A "targeting moiety" is the portion of an immunoconjugate, such as an immunotoxin, intended to target the immunoconjugate to a cell of interest. Typically, the targeting moiety is an antibody, a scFv, a dsFv, an Fab, or an F(ab')2.

A "toxic moiety" is the portion of a immunotoxin which renders the immunotoxin cytotoxic to cells of interest.

As used herein, "cytotoxicity" refers to the toxicity of an immunotoxin to the cells intended to be targeted by the immunotoxin, as opposed to the cells of the rest of an organism. Unless otherwise noted, in contrast, the term "toxicity" refers to toxicity of an immunotoxin to cells others than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

The term "mesothelin" includes reference to a mesothelin protein and fragments thereof which may be present on the surface of one or more cells of a mammal, such as a rat, a mouse, a primate, or, in particular, a human. The preferred nucleic acid and amino acid sequences of mesothelin are as described in PCT published application WO 97/25,068, U.S. application Ser. No. 08/776,271 and U.S. Provisional Application 60/010,166. In addition, see, Chang, K. & Pastan, I., *Int. J. Cancer* 57:90 (1994); Chang, K. & Pastan, I., *Proc. Nat'l Acad. Sci. USA* 93:136 (1996); Brinkmann U., et al., *Int. J. Cancer* 71:638 (1997); and Chowdhury, P. S., et al., *Mol. Immunol.* 34:9 (1997).

As used herein, the term "anti-mesothelin" in reference to an antibody, includes reference to an antibody which is generated against mesothelin. In preferred embodiments, the mesothelin is a primate mesothelin such as human mesothelin. In a particularly preferred embodiment, the antibody is generated against human mesothelin synthesized by a non-primate mammal after introduction into the animal of cDNA which encodes human mesothelin.

The term "anti-Tac" refers to a monoclonal antibody which binds to the IL-2 receptor. IL-2 is a polypeptide hormone which mediates activation of human T cells through binding to the IL-2 receptor (IL-2R). Anti-Tac has been known since at least 1982 (see, e.g., Depper et al., J. Immunol., 131:690-696 (1983)), and has been used for more than a decade in trials to treat individuals with T-cell leukemia and other disorders (e.g., Waldmann et al., Blood, 72:1805-1816 (1988)).

The term "B3" refers to a murine antibody directed against a carbohydrate antigen in the Lewis$^Y$ family. See, e.g., Pastan et al., Cancer Res. 51:3781-3787 (1991);WO 96/13594. Lewis$^Y$ antigens are found on the surface of many mucinous carcinomas of the colon, stomach, ovaries, breast, lung, as well as some epidermal carcinomas. Id. In some preferred embodiments, the term "B3" refers to humanized forms of the B3 antibody, as described in WO 96/13594.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table A each contain amino acids that are conservative substitutions for one another:

TABLE A

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W. H. Freeman and Company, New York (1984).

For purposes of this application, amino acids are classified as acidic or basic, or as negatively or positively charged, depending on their usual charge at neutral pH (physiological pH is generally considered to be about 7.4). Lysine and arginine are basic amino acids which carry a positive charge at neutral pH. Aspartic acid and glutamic acid are acidic amino acids that carry a negative charge at neutral pH. Three other amino acids, histidine (which can be uncharged or positively charged depending on the local environment), cysteine, and tyrosine, have readily ionizable side chains, see generally, Stryer, L. *Biochemistry*, W. H. Freeman and Co., New York (4$^{th}$ Ed., 1995); however, cysteine and tyrosine are only positively charged at higher pH and are not considered basic residues for purposes of the methods taught herein.

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "liking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g. promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression cassette" refers to a recombinant nucleic acid construct comprising an expression control sequence operatively linked to an expressible nucleotide sequence. An expression cassette generally comprises sufficient cis-acting elements for expression; other elements for expression can be supplied by the host cell or in vitro expression system.

"Expression vector" refers to a vector comprising an expression cassette. Expression vectors include all those known in the art, such as cosmids, plasmids (e.g. naked or contained in liposomes) and viruses that incorporate the expression cassette.

A first sequence is an "antisense sequence" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al, eds 1995 supplement)).

One example of a useful algorithm is PILEUP. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithms that are suitable for determining percent sequence identity and sequence similarity are the BLAST and the BLAST 2.0 algorithm, which are described in Altschul et al., *J. Mol. Biol.* 215:403-410 (1990) and Altschul et al., *Nucleic Acids Res.* 25:3389-3402 (1977)). Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915 (1989)).

"Stringent hybridization conditions" refers to 50% formamide, 5×SSC and 1% SDS incubated at 42° C. or 5×SSC and 1% SDS incubated at 65° C., with a wash in 0.2×SSC and 0.1%SDS at 65° C.

"Naturally-occurring" as applied to an object refers to the fact that the object can be found in nature. For example, an amino acid or nucleotide sequence that is present in an organism (including viruses) that can be isolated from a source in nature and which has not been intentionally modified by man in the laboratory is naturally-occurring.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier.

"Pharmacologically effective amount" refers to an amount of an agent effective to produce the intended pharmacological result.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON'S PHARMACEUTICAL SCIENCES, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal.

"Administration" of a composition refers to introducing the composition into the subject by a chosen route of administration. For example, if the chosen route is intravenous, the composition is administered by introducing the composition into a vein of the subject.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

Antibodies and Fragments Thereof

The present invention provides antibodies and fragments thereof which retain antigen-binding capability which have reduced toxicity due to site-specific mutations which reduce the pI of the Fv of the antibody. Without wishing to be bound by theory, it is believed that such Fvs have reduced binding to negatively charged groups on the surface of cells in the liver, thereby reducing the uptake of immunotoxin by those cells.

The mutated antibodies generated by the methods taught herein can be linked to a protein toxin molecule, through the toxin's carboxyl terminus, the toxin's amino terminus, through an interior amino acid residue of the toxin, such as cysteine, or any combination thereof. Similarly, the toxin can be linked directly to the heavy, light, Fc (constant region) or framework regions of the antibody. Linkage can occur through the antibody's amino or carboxyl termini, or through an interior amino acid residue. Further, multiple toxin molecules (e.g., any one of from 2-10) can be linked to the antibody and/or multiple antibodies (e.g., any one of from 2-5) can be linked to a toxin. The antibodies used in a multivalent immunotoxin composition of the present invention can be directed to the same or different epitopes.

In preferred embodiments of the invention, the antibody is a recombinant antibody or fragment thereof which retains antigen-binding capability, such as a scFv or a disulfide stabilized Fv antibody. Fv antibodies are typically about 25 kDa and contain a complete antigen-binding site with 3 CDRs per each heavy chain and each light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In some preferred embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced.

In a more preferred set of embodiments, the antibody is a disulfide stabilized Fv (dsFV). In one group of particularly preferred embodiments, the antibodies have $V_L$ and $V_H$ regions having the amino acid sequence set forth in FIG. 2. One of skill will realize that conservative variants of the antibodies of the instant invention can be made. Such conservative variants employed in dsFv fragments or in scFv fragments will retain critical amino acid residues necessary for correct folding and stabilizing between the $V_H$ and the $V_L$ regions, and will retain the charge characteristics of the residues in order to preserve the low pI and low toxicity of the molecules.

In some embodiments of the present invention, the scFv antibody is directly linked to the toxin through the light chain. However, scFv and dsFv antibodies can be linked to the toxin via the amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. Nos. 4,946,778, 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Ser, (SEQ ID NO:45) preferably 2, 3, 4, 5, or 6 such sequences. However, it is to be appreciated that some amino acid substitutions within the linker can be made. For example, a valine can be substituted for a glycine.

Monoclonal antibodies suitable for modification by the methods taught herein may be obtained by various techniques familiar to those skilled in the art. Description of techniques for preparing such monoclonal antibodies may be found in, e.g., Stites, et al. (eds.) Basic and Clinical Immunology (4th ed.), Lange Medical Publications, Los Altos, Calif., and references cited therein; Harlow & Lane, Antibodies, A Laboratory Manual, Cold Spring Harbor Publications, New York (1988); Goding, Monoclonal Antibodies: Principles and Practice (2d ed.), Academic Press, New York, N.Y. (1986); Kohler & Milstein, *Nature* 256:495-497 (1975); and particularly (Chowdhury, P. S., et al., *Mol. Immunol.* 34:9 (1997)), which discusses one method of generating monoclonal antibodies.

It is preferred that parental monoclonal antibodies are made by immunizing an animal with the target antigen or with nucleic acid sequence that encodes the desired immunogen. Immunization with non-replicating transcription units that encode a heterologous proteins elicits antigen specific immune responses. After translation into the foreign protein, the protein is processed and presented to the immune system like other cellular proteins. Because it is foreign, an immune response is mounted against the protein and peptide epitopes that are derived from it (Donnelly, et al., *J. Immunol. Methods* 176:145-152 (1994); and Boyer, et al., *J. Med. Primatol.* 25:242-250 (1996)). This technique has two significant advantages over protein-based immunization. One is that it does not require the purification of the protein, which at best, is time consuming and in cases of many membrane proteins, is very difficult. A second advantage is that since the immunogen is synthesized in a mammalian host, it undergoes proper post-translational modifications and folds into the native structure.

To immunize with DNA, cDNA coding for the antigen of interest is introduced into a plasmid so that transcription of the coding sequence is under the control of a promoter such as the CMV promoter. The plasmid is then injected into an animal, either subcutaneously, intradermally, intraperitoneally, etc. As a result, the cDNA is transcribed in the animal into mRNA, protein is translated from the mRNA, the translated protein undergoes proper post-translational modifications and is expressed on the surface of cells which synthesized the protein. The animal raises antibodies to the protein and the sera is monitored for antibody titer.

Optionally, in addition to the coding region and regulatory elements, the plasmid carries an ampicillin resistance (Amp) gene. The Amp gene is known to have immunostimulatory sequences for Th1 responses necessary for increased antibody production (Sato, et al., *Science* 273:352-354 (1996)).

As described above, in preferred embodiments, the monoclonal antibody is a scFv or dsFv. Methods of making scFv antibodies have been described. See, Huse, et al., supra; Ward, et al. *Nature* 341:544-546 (1989); and Vaughan, et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes. The scFv can be converted to a dsFv by engineering in cysteine residues to permit formation of a disulfide bond.

In a preferred embodiment, scFv are chosen through a phage display library. For convenience, the discussion herein will describe the process using mesothelin as an example; the same process can, however, be used for other antigens of choice. The procedure described above for synthesizing scfv is followed. After amplification by PCR, the scFv nucleic acid sequences are fused in frame with gene III (gIII) which encodes the minor surface protein gIIIp of the filamentous phage (Marks, et al., *J. Biol. Chem.* 267:16007-16010 (1992); Marks, et al., *Behring Inst. Mitt.* 91:6-12 (1992); and Brinkmann, et al., *J. Immunol. Methods* 182:41-50 (1995)). The phage express the resulting fusion protein on their surface. Since the proteins on the surface of the phage are functional, phage bearing mesothelin-binding antibodies can be separated from non-binding or lower affinity phage by panning or antigen affinity chromatography (McCafferty, et al., *Nature* 348:552-554 (1990)).

In a preferred embodiment, scFv that specifically bind to mesothelin are found by panning. Panning is done by coating a solid surface with mesothelin and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to mesothelin coated plates are expanded in *E. coli* and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with large libraries of clones.

As is well known in the art, cells are bounded by cell membranes which have an intracellular face and an extracellular face or surface. Persons of skill in the art will appreciate that antigens to be bound by the recombinant immunotoxin of the invention are preferably expressed on the exterior surface of the target cell so that the antigen is accessible to the antibody or antigen-binding fragment thereof that is the targeting moiety of the recombinant immunotoxins of the invention. Many such antigens, including the IL-2 receptor, mesothelin, and Lewis$^Y$ antigen, are known in the art.

Production of Immunotoxins

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie A G, Buchs, Switzerland), Invitrogen, San Diego, Calif., and Applied Biosystems (Foster City, Calif.), as well as many other commercial sources known to one of skill.

Nucleic acids encoding native toxins or antibodies such as anti-mesothelin, anti-Lewis$^Y$ antigen, or anti-TAC antibodies can be modified to form the immunotoxins of the present invention. Modification by site-directed mutagenesis is well known in the art. In a preferred embodiment, site-directed modification is conducted by the method of Kunkel, T. A., *Proc. Natl. Acad. Sci.* (USA) 82:488-492 (1985), modified as set forth in the Examples. Nucleic acids encoding toxins or antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunotoxins are prepared by inserting the cDNA which encodes an appropriate antibody into a vector which comprises the cDNA encoding a protein toxin. The insertion is made so that the dsfv or scFv and the toxin moiety are read in frame, that is in one continuous polypeptide which contains a functional Fv region and a functional toxin region. In a more preferred embodiment, cDNA encoding a *Pseudomonas* exotoxin fragment is ligated to a dsFv or scFv so that the toxin is located at the carboxyl terminus of the scFv. In some preferred embodiments, cDNA encoding a cytotoxic fragment of PE, such as PE38, is ligated to a dsFv so that the toxin is located at the amino terminus of the dsFv.

Once the nucleic acids of interest are isolated and cloned, one may express the desired protein in a recombinantly engineered cell such as bacteria, plant, yeast, insect and mammalian cells. It is expected that those of skill in the art are knowledgeable in the numerous expression systems available for expression of proteins, including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., immunotoxins in which the Fv of an anti-body or fragment specifically mutated to reduce pI) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. DNA sequences encoding the M16, St6, and Mt9 Fvs are set forth in Example 7. One of skill will also recognize that due to the degeneracy of the genetic code, the Fvs, and the recombinant immunotoxins of the invention, can be encoded by a large number of nucleic acid sequences.

In addition to recombinant methods, the immunotoxins of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

B. Purification

Once expressed, the recombinant immunotoxins of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g. 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

*Pseudomonas* Exotoxin and Other Toxins

Toxins are employed with antibodies or fragments thereof to yield the recombinant immunotoxins of the invention. Exemplary toxins include ricin, abrin, Diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al, *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin A. Native *Pseudomonas* exotoxin A ("PE") is an extremely active monomeric protein (molecular weight 66 kD), secreted by *Pseudomonas aeruginosa*, which inhibits protein synthesis in eukaryotic cells. The term "*Pseudomonas* exotoxin" as used herein refers to a PE that has been modified to remove or to reduce non-specific binding. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:43) and REDL (SEQ ID NO:44). See Siegall, et al., *J. Biol. Chem.* 264:14256-14261 (1989). In a preferred embodiment, the cytotoxic fragment of PE retains at least 50%, preferably 75%, more preferably at least 90%, and most preferably 95% of the cytotoxicity of native PE. In particularly preferred embodiments, the cytotoxic fragment is more toxic than native PE.

The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain Ib (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., (1989), supra.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or preprotein). Cytotoxic fragments of PE known in the art include PE40, PE38, and PE35.

In preferred embodiments, the PE has been modified to reduce or eliminate non-specific cell binding, frequently by deleting domain Ia as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art. See, Pai, et al., *Proc. Nat'l Acad. Sci. USA* 88:3358-62 (1991); and Kondo, et al., *J Biol. Chem.* 263: 9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)).

While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (e.g., a similar charge).

Pharmaceutical Compositions and Administration

The immunotoxins of this invention, are particularly useful for parenteral administration, such as intravenous administration or administration into a body cavity or lumen of an organ. For example, ovarian malignancies may be treated by intravenous administration or by localized delivery to the tissue surrounding the tumor of an anti-mesothelin-targeted immunotoxin, such as St6 ds(Fv)-PE38. To treat mesotheliomas, pharmaceutical compositions of this invention comprising immunotoxins targeted by anti-mesothelin antibodies can be administered directly into the pleural or peritoneal cavities. Immunotoxins targeted by an anti-Tac antibody or fragment thereof or an anti-Lewis$^Y$ antibody or fragment thereof can similarly be administered by intravenous administration.

The compositions for administration will commonly comprise a solution of the immunotoxin dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunotoxin compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp.315-339, (1992) both of which are incorporated herein by reference.

Polymers can be used for ion-controlled release of immunotoxin compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. For example, one preferred application for the immunotoxins of the invention is the treatment of malignant cells expressing mesothelin. Exemplary malignant cells include ovarian, stomach and squamous cell cancers as well as mesotheliomas. Similarly, anti-Tac based immunotoxins can be used in T-cell malignancies and anti-LewisY antigen antibodies can be used for to kill cells of LewisY antigen-bearing carcinomas of the colon, stomach, ovaries, breast, lung and other tissues. Administration of the immunotxins permits them to contact cells bearing antigens recognized by the targeting moiety of the immunotoxin (the antibody or fragment thereof), permitting the immunotoxin to be internalized and to kill the cell.

EXAMPLES

Example 1

This Examples sets forth the materials and methods used in Example 2.

Calculated pI Value of Fv

The pI of each Fv was calculated using a program in the Genetics Computer Group (Madison, Mich.) package that is available through the web site http:/molbio.info.nih.gov/molbio/gcglite/protform.htm. In the Fv portion, cysteines have no charge because they are disulfide bonded. These were converted to serine for the pI calculation. LMB.2 has a high pI (10.21), whereas the pI of RFB4 is 7.67.

Modeling of Electrostatic Potential

Electrostatic potential was mapped to the molecular surface of wild-type and M1-mutant models of anti-Tac(Fv). The models of the wild-type and mutant were produced using GRASP (Nicholls, A. et al., Proteins Struct. Funct. Genet. 11:281 (1991)) and Ribbons (Carson, M. J. Appl. Crystallogr. 24:958 (1991)) and were generated by homology modeling starting from the crystal structure of McPC603, a phosphocholine-binding mouse myeloma protein (Rudikoff, S., et al., Mol. Immunol. 18:705 (1981)).

Anti-Tac(Fv)-PE38 Mutagenesis

Mutagenesis of anti-Tac(Fv)-PE.38 was done by Kunkel's method (Kunkel, T., Proc Natl Acad Sci (USA), 82: 488-492 (1985)) with some modification. C1 236 cells were transformed with pRK79. After selection on Lauria-Bertani plates containing 2% glucose, 30 µg/ml chloramphenicol, and 100 µg/ml ampicillin, the transformants were grown in 2× YT medium containing glucose and the antibiotics, as mentioned above, and 0.025% uridine at 37° C. At an $OD_{600}$ of 0.36, the cells were infected with the helper phage M13 as a multiplicity of infection of 5. After incubation at 37° C./110 rpm for 1 h, the culture was maintained at 37° C./300 rpm for another 6 h. The bacterial cells then were precipitated by centrifugation and the phage from the supernatant was precipitated with polyethylene glycol. The single-stranded, uracil-containing DNA from the purified phage was extracted with phenol and chloroform and precipitated with lithium chloride and chilled ethanol as final concentrations of 0.8 M and 75%, respectively. This ssDNA codes for the sense strand of anti-Tac(Fv)-PE38. The following primers were used for anti-Tac(Fv)-PE38 mutagenesis:

M1 $V_L$ Q1D, 5'-TGCTGGAGACTGGGTGAGAACGATAT-CAGAGCCG CCGCCACCCGAGCCGCCACCGC-CCGAGCCACC-3' (SEQ ID NO:21); M1 $V_L$ Q1D+$V_L$ V3E, 5'-GATTGCTGGAGACTGGGTGAGTTC-GATATCAGAGCCGC CGCCACCCGAGCCGCCAC-CGCCCGAG-3' (SEQ ID NO:22); M1 $V_L$ S70D, 5'-GCT GATTGTGAGAGAGTAATCGGTCCCG-GATCCACTGCCACTGCCACGAAG CG-3' (SEQ ID NO:23); M1 $V_L$ S100D, 5'-TTTGAGCTCCAGCTTGGTAC-CATCACCGAAC GTGAGTGGGTA-3' (SEQ ID NO:24); M1 $V_H$ Q1E, 5'- TGAGGCCCCAGGTTTTGCTAGCT-CAGCCCCAGACTGCTGCAGATGGACCTCCATA TGTATATCTCC-3' (SEQ ID NO:25); M1 $V_H$ Q6E, 5'-TGAGGCCCCAGGTTTTGCTAGC TCAGCCCCA GACTCCTGCAGATGGACCTGCAT-3' (SEQ ID NO:26); M1 $V_H$ Q1E+H3Q+Q5V+Q6E, 5'-TGAGGCCCCAG-GTTTTGCTAGCTCAGCCCC AGACTCCACCAGT TGGACCTCCATATGTATATCTCC-3' (SEQ ID NO:27); and M1 $V_H$ G42E, 5'-AATCCAT TCCAGACCCTGTTCAG-GTCTCTGTTTTACCCAGTGCAT-3'(SEQ ID NO:28).

The primers were phosphorylated using polynucleotide kinase and T4 DNA ligase buffer from Boehringer Mannheim (Indianapolis, Ind.). These phosphorylated primers were used to introduce the mutations in the uracil template of pRK79 using Bio-Rad (Richmond, Calif.) Muta-Gene kit. The product at the end of the mutagenesis reaction was used to directly transform DH5α competent cells. Minipreps were made from single colonies and analyzed with the restriction enzymes, sites which had been introduced by the primers for mutagenesis. Mutations in the clones were confirmed by automated DNA sequencing.

Production of Recombinant Protein

The components of anti-Tac(Fv)-PB38 and 10 mutants were expressed in *Escherichia coli* BL21(λDE3) and accumulated in inclusion bodies as previously described for other recomobinant immunotoxins (Kreitman et al., Int. J. Cancer 81:148 (1999) (hereinafter "Kreitman 1999"). Inclusion bodies were solubilized in GuCl, reduced with DTE (dithioerythritol), and refolded by dilution in a refolding buffer containing arginine to prevent aggregation, and oxidized and reduced glutathione redox shuffling (id.). Active monomeric protein was purified from the refolding solution by ion exchange and size exclusion chromatography to near homogeneity as described (id.; Chowdhury, P., et al., Proc Natl Acad Sci USA 95:669 (1998)(hereinafter "Chowdhury1998")), Protein concentrations were determined by Bradford assay (Coomassie Plus; Pierce. Rocklord, Ill.).

Cytotoxicity Assays

The specific cytotoxicity of the anti-Tac(Fv)-PE38 and its mutants was assessed by protein synthesis inhibition assays (inhibition of incorporation of tritium-labeled leucine into cellular protein) in 96-well plates as previously described (Kreitman 1999; Chowdyhury 1998). The activity of the molecule is defined by the $IC_{50}$, the toxin concentration that reduced incorporation of radioactivity by 50% compared with cells that were not treated with toxin. The specificity is obtained by comparing the activity toward Ag-positive cells vs toxicity against Ag-negative cells. Fresh malignant cells were partially purified from patients with B-cell leukemia anti incubated with recombinant toxins as previously described (Kreitman et al., Blood 80:2344 (1992)).

Nonspecific Toxicity Assay

Groups of live female (~20 g) NTH Swiss were given injections i.v. through the tail vein of 200 µl of escalating doses of anti-Tac(Fv)-P238 or its mutant immunotoxins diluted in PBS-human serum albumin ("HSA") (0.2%). Animals were observed 2 wk for mortality. The $LD_{50}$ is the calculated dose of immunotoxin that kills 50% of the animals.

Histological Study

NIH Swiss mice were sacrificed 24 h after injection of immunotoxin. Liver and kidney were fixed by 10% Formaline. Sections from each of these organs were stained with hematoxylin and eosin (H&E) and examined histologically.

Antitumor Activity of Anti-Tac(Fv)-PE38 and M1 (Fv)-PE38 in Nude Mice

Antitumor activity of anti-Tac(Fv)-PE38 and M1(Fv)-PE38 was determined in nude mice bearing ATAC4 cells. These cells ($2.5 \times 10^6$) were injected s.c. into nude mice on day 0. Tumors about 50 $mm^3$ developed in animals by day 4 after tumor implantation. Starting on day 4, animals were treated with i.v. injections of anti-Tac(Fv)-PE38 and M1 (Fv)-PE38 diluted in 0.2 ml of PBS-HSA (0.2%). Therapy was given once every other day (on days 4, 6. and 8) and each treatment group consisted of 5 animals. Tumors were measured with a caliper every 2 or 3 days and the volume of the tumor was calculated by using the formula:

tumor volume ($mm^3$)=length×(width)$^2$×0.4.

Example 2

One group of particularly useful recombinant immunotoxins is composed of Fv fragments of mouse mAbs fused to a 38,000 m.w. form of PE known as PE38. The Fv fragment replaces the binding domain (domain Ia) of native PE and directs the toxin to Ags on cancer cells. Because mouse mAbs are selected by the mouse immune system not to react with mouse antigens ("Ag"), the toxicities that occur in mice that have been administered these recombinant immunotoxins are due to nonspecific interactions of the recombinant immunotoxins with mouse tissues. The data in Table I show the $LD_{50}$ in mice of three different recombinant immunotoxins that are made with three different mouse mAbs, none of which specifically react with mouse cells. Anti-Tac(Fv)-PE38 is targeted at the a subunit of the human IL-2 receptor (CD25) (2, 11). SS(Fv)-PE38 is targeted at an Ag termed "mesothelin" that is found on mesothelial cells, ovarian cancers, and mesotheliomas (Chowdhury 1998). RFB4(Fv)-PE38 is targeted to CD22. The data in Table I show that when a single dose of each of the recombinant immunotoxins is injected i.v. in mice, the $LD_{50}$s vary widely. The most toxic is anti-Tac (Fv)-PE38 with an $LD_{50}$ of 0.34 mg/kg. The least toxic is RFB4(Fv)-PE38 which has an $LD_{50}$ of 0.81 mg/kg. SS(Fv)-PE38 has intermediate $LD_{50}$ of 0.68 mg/kg. These three molecules are identical in the PE portion but vary in the Fv. Thus, we concluded that these differences in toxicity were due to some different property in the Fv. The data in Table I also show pI of the Pv portion of these recombinant immunotoxins. They vary widely from a pI of 10.2 for anti-Tac(Fv) to a pI of 7.67 for RFB4(Fv). The PE portion of the molecules is rather acidic, with a pI of 5.4. Thus the nonspecific toxicity increases with the pI of the Fv moiety. The cause of death resulting from injection of all these immunotoxins is acute hepatic necrosis. Therefore, the toxicity in mice could be due to some direct interaction of the Fv portion of the recombinant immunotoxins with the liver. Because the liver cell membranes have a negative charge, the positive charge at neutral pH on the Fv portion of the recombinant immunotoxins could favor higher nonspecific binding and uptake of the recombinant immunotoxins by cells in the liver. If this were the case, one should be able to decrease the toxicity of anti-Tac(Fv)-PE38 and other Abs by decreasing their pI by site-directed mutagenesis of the framework regions leaving the CDRs intact and, therefore, not affect the specific interactions of the Ab, such as anti-Tac(Fv)-PE38, with the antigen target.

To test this hypothesis, the amino acid sequence of the Fv portion of anti-Tac was compared with the Fv portion of RFB4 and the number of charged amino acids determined. RF84(Fv) has 10 lysines, 7 arginines, 10 aspartates, 8 glutamates, and 2 histidines, whereas anti-Tac(Fv) has 13 lysines, 6 arginines, 5 aspartates, 8 glurtmates, and 3 histidines (Table II). The differences in positive and negative residues are responsible for the differences in the pI between RFB4(Fv) and anti-Tac(Fv). Therefore, making anti-Tac(Fv) more like RFB4(Fv) could reduce the pI of anti-Tac(Fv). Accordingly, the RFB4 and anti-Tac(Fv) sequences were aligned and several surface-exposed residues in the framework region in anti-Tac(Fv) were mutated to make them resemble sequences in RFB4(Fv). This had the effect of lowering the pI. Initially, a series of recombinant immunotoxins was made in which single residues were mutated to acidic residues one at a time. The residues in anti-Tac that were changed are Q1, V3, S70, and S100 of $V_L$; and Q1 and G42 of $V_H$ (Table III). In general, the residues were changed to aspartate or glutamate. In addition, mutations H3Q, Q5V, and Q6E were introduced in the $V_H$ to make the amino terminus more closely resemble the amino terminus of RFB4. After these single-residue mutants were analyzed for cytotoxicity and mouse toxicity, two more recombinant immunotoxins (M1 and M2) were constructed in which mutations were combined (see Table III).

Expression and Purification of Single-Chain Recombinant Immunotoxins

Overall, 10 mutants of anti-Tac(Fv)-PE38 were constructed. The mutations were confirmed by DNA sequencing and the recombinant proteins were expressed in *E. coli*. where they all accumulated in inclusion bodies. All immunotoxins were purified by ion-exchange and size-exclusion chromatography from renatured inclusion bodies. Each of the 11 immunotoxins (10 mutants and 1 wild type) eluted as a monomer upon TSK gel-filtration chromatography and migrated as a single, major band of about 63 kDa in SDS-PAGE (data not shown). The data in Table IV show the activity of each of the mutant molecules on Ag-positive ATAC-4 cells that express CD25 and the calculated pI of the Fv portion. All of the molecules constructed had the same activity on ATAC-4 cells. Therefore, by introducing negatively charged residues, there was no loss of specific cylotoxic activity on target cells expressing human IL-2Rα. Introduction of single negatively charged residues lead to only a small decrease in the calculated pI. Introduction of one or two negatively charged residues also led to a small decrease of pI from 10.2 to 9.95. Only when several mutations were combined did the pI fall significantly. The pI fell to 6.82 for mutant M1 and to 7.76 for mutant M2.

Then each of these molecules was evaluated for as nonspecific toxicity in mice (Table IV). Groups of five mice or more were injected with varying doses of immunotoxin and observed for 2 wk. Almost all of the deaths occurred within 72 h after treatment. In general, single amino acid changes did not produce large changes in mouse toxicity, although both the decreases and increases in nonspecific mouse toxicity were observed by single mutations. However, when all of the mutations were combined into one molecule to produce scM1, which had a pI of 6.82, the single-dose toxicity in mice was greatly diminished; the $LD_{50}$ rose from 0.34 mg/kg to 1.22 mg/kg. Mutant M2 has a pI of 7.76 and contains all the mutations found within M1 except for the G42E mutation in $V_H$. The animal toxicity ($LD_{50}$) of M2(Fv)-PE38 is 0.56 mg/kg, which is intermediate between the toxicity of anti-Tac (Fv)-PE38 and MI(Fv)-PE38.

Liver Toxicity

To determine the cause of death, mice were sacrificed 24 h after administration of 9 μg (0.45 mg/kg) of anti-Tac(Fv)-PE38 or M1(Fv)-PE38 and sections of the livers were prepared and stained with H&E. In the mice treated with anti-Tac(Fv)-PE38, there was evidence of severe hemorrhagic liver necrosis, whereas the livers from the mice treuted with M1(Fv)-PE38 appeared normal. The finding of hemorrhagic necrosis raises the possibility that the liver endothelial cells are being damaged as part of the process of liver toxicity.

Additional Cytotoxic Properties of M1(Fv)-PE38

M1(Fv)-PE38 was selected for further study because of its low animal toxicity. Before doing further animal studies, its cytotoxic activity on several other cell lines was investigated (Table V). HUT102 is a cell line from a patient with adult T cell leukemia. Anti-Tac(Fv)-PE38 and M1(Fv)-PE38 had similar cytotoxic activities on this cell line with an $IC_{50}$ value of 0.1 ng/ml. Raji is a cell line of B cell lineage that does not express IL-2 receptors. Neither immunotoxin was active at 1000 ng/ml. A431 cells, which do nor have receptors and are the parent of ATAC4, were also examined. The $IC_{50}$ was 390 ng/ml for anti-TacFv)-PE38 and 510 ng/ml for M1(Fv)-PE38.

These very high $IC_{50}$ values, compared with the $IC_{50}$ of 0.07 ng/ml on ATAC4 cells, indicate that the cytotoxic activities of both molecules are highly specific. To determine whether M1(Fv)-PE38 would retain cytotoxicity toward malignant target cells directly obtained from patients, it was incubated with peripheral blood mononuclear cells from two patients with $CD25^+$ B-cell leukemias. In both patients the malignant cells composed >95% of the cell sample tested. As shown in Table V, there was no significant difference in the cytotoxic activity of the two immunotoxins, indicating that the mutations which lowered the pI did not impair cytotoxicity or stability of the protein during its interaction with fresh malignant patient cells.

Antitumor Activity

Figure 1:
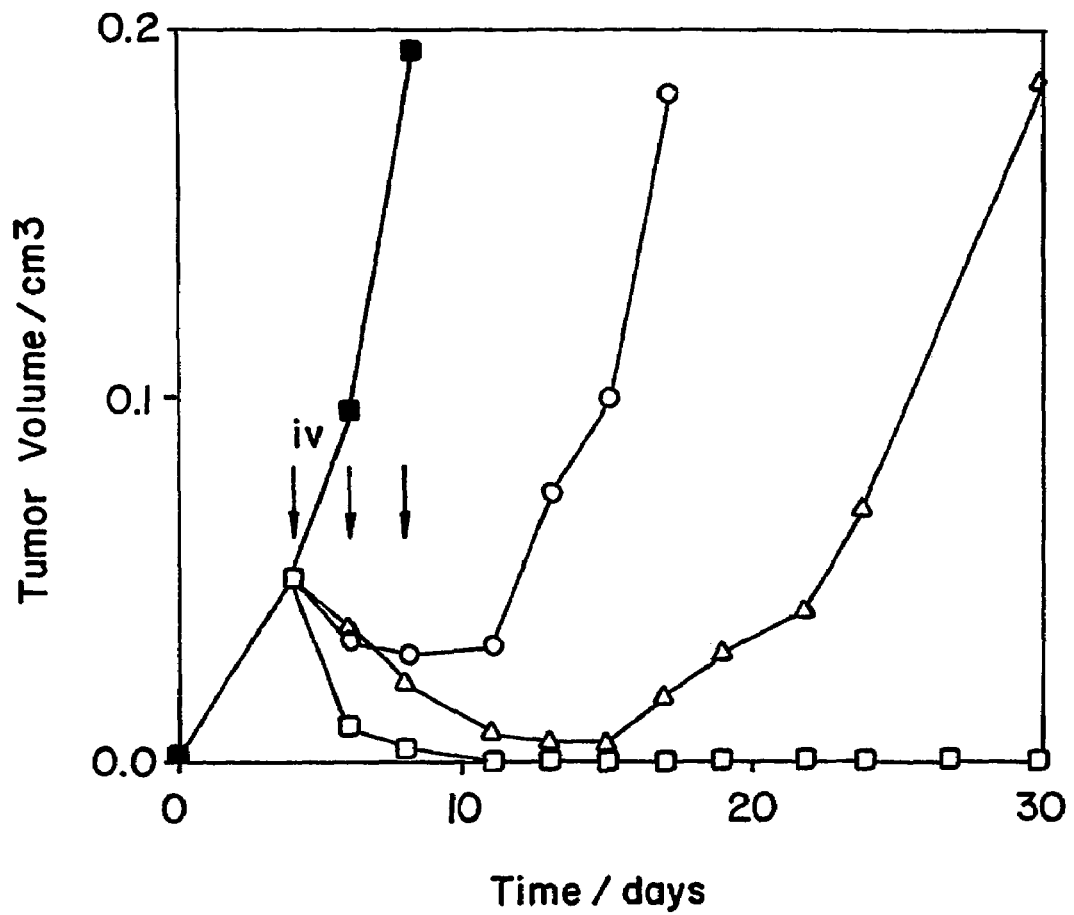
FIG. 1. Anti-tumor effect of M1(Fv)-PE38 in nude mice. Open circles: animals treated with 0.025 mg/kg, triangles: animals treated with 0.075 mg/kg, open squares: animals treated with 0.3 mg/kg of M1(Fv)-PE38 in Dulbecco's modified PBS containing 0.2% HSA. Filled squares: control animals receiving carrier only.

To evaluate antitumor activity, mice were implanted s.c. on day 0 with ATAC4 tumor cells and i.v. therapy was initiated on day 4 using increasing doses of anti-Tac(Fv)-PE38 or M1(Fv)-PE38. Each agent was given every other day for three doses. Typical tumor regression results are illustrated in FIG. 1 for mice treated with increasing doses of M1(Fv)-PE38. Groups of five mice were injected with $2.5 \times 10^6$ ATAC4 cells on day 0. On day 4, tumors reached a size of 0.05 cm3. Animals were treated i.v. on days 4, 6, and 8 with 0.025 mg/kg (○), 0.075 mg/kg (Δ), or 0.3 mg/kg (□) of M1(Fv)-PE38 in Dulbecco's modified PBS containing 0.2% HAS. Control group received carrier alone (■). No death or toxicity was observed at these doses.

The data in Table VI shows the toxicity at each dose level and a summary of tumor responses. The data confirm that anti-Tac(Fv)-PE38 is much more toxic to mice than M1(Fv)-PE38. With anti-Tac(Fv)-PE38, 1 of 15 animals died at 0.075 mg/kg×3; 2 of 15 died at 0.15 mg/kg×3; and all 15 died at 0.3 mg/kg×3. In contrast, there were no deaths with M1(Fv)-PE38 even at 0.5 mg/kg×3. Thus, the three-dose toxicity results in nude mice confirm the one-dose study in normal mice showing that M1(Fv)-PE38 is much less toxic than anti-Tac(Fv)-PE38. The effect of the two immunotoxins on tumor size is also shown in Table VI. The molecules were equally active at the 0.075 mg/kg×3 and 0.15 mg/kg×3 doses, producing 6 of 15 or 7 of 15 complete regressions ("CRs") at the lower dose, and 11 of 15 and 14 of 15 CRs at the higher dose. At the dose levels where anti-Tac(Fv)-PE38 caused deaths, M1(Fv)-PE38 produced 14 of 15 CRs (0.3 mg/kg) and 5 of 5 CRs (0.5 mg/kg). These data clearly show the usefulness of being able to give higher doses of immunotoxin.

Example 3

The procedure discussed in Example 2 showed that the nonspecific toxicity of the recombinant immunotoxin anti-Tac(Fv)-PE38 was reduced by introducing mutations in the Fv portion that lower the pI from 10.21 to 6.82.This was accomplished without altering residues in the complementarity-determining regions, and therefore did not affect the specific cytotoxic effect of the immunotoxin on target cells expressing CD25. As a consequence, tumor-bearing mice could be treated with higher doses and enhanced antitumor activity demonstrated.

Framework residues were changed so that Ag binding would not be affected. Residues were selected that differed between the Fv of mAb RFB4 and that of anti-Tac because RFB4(Fv), which has a pI of 7.67, was much less toxic to mice than anti-Tac(Fv)-PE38 (Table II). In this approach, only one marginally basic residue, was changed, $V_H$H3; this change was not expected alter the pI, because histidine should be largely unprotonated at pH 7.2, which is the pH at the surface of the cells in the liver. The data in Table II show that most of the changes were from neutral to acidic residues. The effect of changing basic residues to acidic or neutral residues is demonstrated in Examples 4-6, below. A compilation of the frequency with which each amino acid is present in the framework regions of $V_H$ and $V_L$ (13) was made. Many residues are highly conserved and were not changed because such mutations might affect Fv folding or stability. Only framework residues which are variable and which lie on the surface of the molecule were chosen so they would not affect protein folding or stability. To examine the effects of the change in pI on the electrostatic potential of the surface of anti-Tac(Fv), a model of the Fv portion of the Ab was employed. The electrostatic potential mapped to the molecular surface of wild-type and M1-mutant models of anti-Tac(Fv). A large increase in the negative potential was noted on both the front and back sides of the M1 mutant.

Several investigators have shown that when Abs or albumin are cationized by treatment with an amine, their pharmacokinetic properties are altered and their uptake by liver and other tissues is greatly enhanced (Pardridge et al., J. Pharmacol. Exp. Ther. 286:548 (1998); Pardridge et al., J. Pharm Sci., 84:943 (1995); Pardridge et al., J. Pharmacol. Exp. Ther. 276:246 (1996)). These data are consistent with the findings of the present study. The positive charge in the Fv would appear not only to enhance liver uptake, but also uptake by other organs. Alterations in animal toxicity could also be due to changes in half-life and stability.

The toxic side effects of immunotoxins in animals and humans are of two types. One side effect arises from the targeted killing of normal cells that have the same Ag as the tumor cells. The best solution to overcome this toxicity is to find a different target Ag that is not expressed on normal cells. The second type of toxicity arises from undefined nonspecific binding to normal cells. The liver is particularly vulnerable because it is susceptible to apoptosis induced by toxic substances, it has a high blood content, and its capillaries are fenestrated allowing immediate access of the high concentrations of immunotoxins that are in the blood just after injection. However, capillary damage could also occur, leading to hemorrhagic liver necrosis and also contributing to the vascular leak syndrome that has been observed with immunotoxins containing ricin as well as those containing PE (Soler-Rodriguez et al., Exp. Cell Res. 206:227 (1993); Kuan et al., Clin. Cancer Res. 1:1589 (1995)).

In sum, the nonspecific toxicity of anti-Tac(Fv)-PE38 (LMB-2) was decreased in mice by about 3-fold without decreasing its specific cellular or antitumor activity. It is therefore expected that the nonspecific toxicity of the immunotoxin in man will likewise be decreased without affecting antitumor activity. This is expected to greatly increase the clinical response to anti-Tac(Fv)-PE38, which ready has shown good antitumor activity in patients with $CD25^+$ leukemias and lymphomas (Krietman and Pastan, Adv. Drug Delivery Res. 31:53 (1998)).

TABLE I

Toxicity and isoelectric point of three single-chain immunotoxins[a]

| Immunotoxin | pI of scFv | $LD_{50}$ (mg/km) |
| --- | --- | --- |
| Anti-Tac(Fv)-PE38 | 10.21 | 0.34 |
| SS(Fv)-PE38 | 8.91 | 0.68 |
| RFB4(Fv)-PE38 | 7.67 | 0.81 |

[a]In comparing the toxicity f immunotoxins at the same dose level, significant differences from anti-Tac(Fv)-PE38 are present (p < 0.001. $X^2$ test).

TABLE II

Number of charged residues in Fvs of anti-Tac, RFB4. and M1

| Fv | V_L | | | | | V_H | | | | | pI |
|---|---|---|---|---|---|---|---|---|---|---|---|
| | K | R | E | D | H | K | R | E | D | H | |
| RFB-4 | 4 | 3 | 3 | 6 | 1 | 6 | 4 | 5 | 4 | 1 | 7.67 |
| Anti-Tac | 5 | 3 | 4 | 1 | 2 | 8 | 3 | 4 | 4 | 1 | 10.21 |
| M1 | 5 | 3 | 5 | 4 | 2 | 8 | 3 | 7 | 4 | 1 | 6.82 |

TABLE III

The location of amino acids that were mutated in M1[a]

| | $V_h$ | | | | | | | SEQ ID NO: | $V_L$ | | | | | |
|---|---|---|---|---|---|---|---|---|---|---|---|---|---|---|
| | 1 | 2 | 3 | 4 | 5 | 6 | • | | 42 | 1 | 2 | 3 | • 70 • | 100 |
| RFB-4 | E | V | Q | L | V | E | | 46 | E | D | I | Q | D | G |
| Anti-Tac | Q | V | H | L | Q | Q | | 47 | G | Q | I | V | S | S |
| M1 | E | | Q | | V | E | | — | | E | D | E | D | D |

[a]Numbering is according to Kabat et al.

TABLE IV

Mutations in the Fv portion of anti-Tac(Fv)-PE38, cytotoxic activity on ATAC4 cells, mouse toxicity, and pIs[a]

| Fv Mutations | $IC_{50}$(ng/ml) | $LD_{50}$ (mg/kg) | pI of Fv |
|---|---|---|---|
| None | 0.07 ± 0.02 | 0.34 | 10.21 |
| $V_L$ Q1D | 0.07 ± 0.02 | 0.32 | 10.09 |
| $V_L$ Q1D, V3E | 0.07 ± 0.02 | 0.24 | 9.95 |
| $V_L$ S70D | 0.07 ± 0.02 | 0.46* | 10.09 |
| $V_L$ S100D | 0.07 ± 0.02 | 0.22‡ | 10.09 |
| $V_H$ Q1E | 0.05 ± 0.02 | 0.25 | 10.09 |
| $V_H$ Q6E | 0.05 ± 0.02 | 0.25† | 10.09 |
| $V_H$ Q1E, H3Q, Q5V, Q6E | 0.07 ± 0.02 | 0.46 | 9.95 |
| VH G42E | 0.07 ± 0.02 | 0.17 | 10.09 |
| M2 ($V_H$ Q1E, H3Q, Q5V, Q6E) ($V_L$ Q1D, V3E, S70D, S100D) | 0.07 ± 0.02 | 0.56* | 7.76 |
| M1 (($V_H$ Q1E, H3Q, Q5V, Q6E, G42E) ($V_L$ Q1D, V3E, S70D, S100D) | 0.07 ± 0.02 | 1.22* | 6.82 |

[a]Agents significantly less toxic than unmodified anti-Tac(Fv)-PE38 by $\chi^2$ analysis are indicated: *. p < 0.001; †p < 0.005; ‡. p < 0.01. Based on comparison of toxicity results at different dose levels, M1 was 3-fold less toxic than LMB-2 at a significance level of p < 0.025 and was 2.7-fold less toxic at a significance level of p < 0.001.

TABLE V

Activity of anti-Tac(Fv)-PE38 on cell lines

| | | $IC_{50}$ (ng/ml) | |
|---|---|---|---|
| Cells | Type | scM1 | anti-Tac(Fv)-PE38 |
| ATAC4 | Epidermoid | 0.07 ± 0.02 | 0.07 ± 0.02 |
| HUT102 | ATL | 0.1 ± 0.02 | 0.1 ± 0.02 |
| A431 | Epidermoid | 510 ± 90 | 390 ± 10 |
| SP2/Tac | Plasmacytoma | 0.08 ± 0.005 | 0.08 ± 0.006 |
| Raji | Burkitt's Lymphoma | >1000 | >1000 |
| Patient 1 | B-cell leukemia | 3 ± 0.3 | 2.5 ± 0.25 |
| Patient 2 | B-cell leukemia | 64 ± 18 | 56 ± 45 |

TABLE VI

Effect of increasing doses of anti-Tac(Fv)-PE38 and scM1(Fv)-PE38 on toxicity and tumor responses in mice[a]

| | Death/Total[b] | PR | CR |
|---|---|---|---|
| Anti-Tac(Fv)-PE38 | | | |
| 0.025 mg/kg × 3 | 0/5 | 5/5 | 0/5 |
| 0.075 mg/kg × 3 | 1/15 | 15/15/ | 7/15 |
| 0.15 mg/kg × 3 | 2/15 | 13/15 | 11/15 |
| 0.3 mg/kg × 3 | 15/15 | NE | NE |
| scM1(Fv)-PE38 | | | |
| 0.025 mg/kg × 3 | 0/5 | 5/5 | 0/5 |
| 0.075 mg/kg × 3 | 0/15 | 15/15 | 6/15 |
| 0.15 mg/kg × 3 | 0/15 | 15/15 | 14/15 |
| 0.3 mg/kg × 3 | 0/15 | 15/15 | 14/15 |
| 0.5 mg/kg × 3 | 0/5 | 5/5 | 5/5 |

[a]CR, complete regression of tumor for a minimum of 4 days; PR, reduction of the sum of the tumor length and width by >50% of pre-treatment values; NE, not evaluable.
[b]Number of mice that died divided by number injected.

Example 4

This Example sets forth the materials and methods used in Examples 5 and 6.

Calculated pI Value

The pI of each immunotoxin was calculated using a program in the Genetics Computer group (Madison, Wis.) package that is available through the worldwide web at molbio-.info.nih.gov/molbio/gcglite/protform.html. In the Fv portion, cysteines have no charge because they are disulfide bonded. These were converted to serine for the pI calculation.

Mutagenesis

Mutagenesis of M1(dsFv)-PE38 was done by Kunkel's method (Kunkel, T., *Proc Natl Acad Sci* (USA), 82: 488-492 (1985)) with some modifications. CJ236 cells were transformed with pOND9-1 and pOND9-2. The transformants were grown in 2×YT medium containing 100 µg/ml ampicillin at 37° C. At an OD600 of 0.36, the cells were infected with the helper phage M13 at a multiplicity of infection of 5. After incubation at 37° C./110 rpm for 1 h, the culture was maintained at 37° C./300 rpm for another 6 h. The bacterial cells were then precipitated by centrifugation and the phage from the supernatant was precipitated with polyethylene glycol. The single-stranded uracil-containing DNA from the purified phage was extracted with phenol/chloroform and precipitated with sodium chloride and ethanol. This ssDNA codes for the sense strand of M1(dsFv)-PE38. The following primers were used for M1 mutagenesis: M1 VL K18Q, 5'GGCACTGCAG-GTTATGGTGACTTGCTCCCCTGGAGATGCAGACAT-3' (SEQ ID NO:29); M1 VL K45Q, 5'-GGATGTGG-TATAAATCC ATAGCTGGGGAGAAGTGCCTGGCTT-3' (SEQ ID NO:30); M1 VL R77N, 5'-GGCAGCATCT-TCAGCCTCCATATTCGAAATTGTGAGAGAGTAATC-GGT-3' (SEQ ID NO:31); M1 VL K103-107E, GTTAG-CAGCCGAATTCTATTCGAGTTCCAGCTCGGTCCCG-CAACCGAACGTGAG-3' (SEQ ID NO:32); M1 VH K13E, 5'-CATCTTCACTGAGGCCCCAGGTTCTGCGAGCTCA GCCCCAGA-3' (SEQ ID NO:33); M1 VH K73D, 5'-GCT-CAGTTGCATGTAGGCAGTACTGGAGGAATCGTCTGC AGTCAA-3' (SEQ ID NO:34). The primers were phosphorylated using polynucleotide kinase and T4 DNA ligase buffer from Boehringer Mannheim Indianapolis, Ind.). These phosphorylated primers were used to introduce mutations in the uracil template of pOND9-1 and pOND9-2 using Bio-Rad (Richmond, Calif.) Muta-Gene kit. The product at the end of the mutagenesis reaction was used to directly transform DH5α competent cells. Mutations in the clones were confirmed by automated DNA sequencing.

To introduce cysteines into the framework regions of M1(scFv)-PE38 for making disulfide bond Fv (dsFv), the following primers were used same way: M1 VL E100C, 5'-GCCGCCCTCGGGACCTGAATTCTATTTGAGCTCCA-GCTTGGT CCCGCCAACCGAACGTGAGTGGGTA-4' (SEQ ID NO:35); M1 $v_H$ G44C, 5'- ATATCCAATCCATTC-CAGACACTGTTCAGGCCTCTGTTTTACCCAGTGCAT-3' (SEQ ID NO36).

Mutagenesis of SS1(dsFv)-PE38 was also done by Kunkel's method. After making the uracil template of pSC7-4 and pSC7-7, the following phosphorylated primers were used for SS1(dsFv)-PE38 mutagenesis: SS1 VL R7D, 5'- CAT-GATTGCTGGATCCTGAGTGAGCTC-3' (SEQ ID NO:37); SS1 VL A80E, 5'-CTGGCAGTAATACGTAGCAT-CATCTTCCTCCTCCACGCTGC-3' (SEQ ID NO:38); SS1 VH Q1EK13Q, 5'-AAGCGCGCAGGCTGCTCGAGCT-CAGGCCCAGACTGCTGCAGTTGTACCTC-CATATGTATATCTC-3' (SEQ ID NO:39); SS1 VH S75QS82BNS84N 5'-TGCAGAGTCTTCATTTTCAAT-TAACCATTACATACTTTTACTTTCTAC-3' (SEQ ID NO:40).

Mutagenesis of B3(dsFv)-PE38 was also done by Kunkel's method. After making the uracil template of pUli 39-1 and pYR38-2, the following phosphorylated primers were used for B3(dsFv)-PE38 mutagenesis: B3 VL L3E, 5'-CAATG-GAGACTGGGTCATCTCCACGTCCATATG-TATATCTCCTTC-3' (SEQ ID NO:41); B3 VL K103D, 5'-CTCGGGACCTCCGGAAGCATCTATTTC-CAGATCTGTCCCACAGCCGAACGT-3' (SEQ ID NO:42).

Production of Recombinant Immunotoxin

The components of immunotoxins were expressed in *Escherichia coli* BL21(λDE3) and accumulated in inclusion bodies as previously described for other immunotoxins (Reiter et al., *Biochemistry*, 33: 5451-5459 (1994)). Inclusion bodies were solubilized in GuCl, reduced with dithioerythritol (DTE) and refolded by dilution in a refolding buffer containing arginine to prevent aggregation and oxidized and reduced with glutathione to facilitate redox shuffling. Active monomeric protein was purified from the refolding solution by ion exchange and size exclusion chromatography. Protein concentrations were determined by Bradford assay (Pierce, Coomassie Plus).

Isoelectric Focusing

The recombinant immunotoxins and standard markers with pI values ranging 4.5-9.6 were analyzed using the Ready Gel System (IEF Ready Gel, Bio-Rad, Richmond, Calif.). These gels were stained by Coomasie Blue R-250 to reveal the protein bands.

Cytotoxicity Assay

The specific cytotoxicity of each IT was assessed by protein synthesis inhibition assays (inhibition of incorporation of tritium-labeled leucine into cellular protein) in 96-well plates as previously described (Brinkmann et al., *Proc Natl Acad Sci* (USA), 88: 8616-8620 (1991)). The activity of the molecule is defined by the $IC_{50}$, the toxin concentration that reduced incorporation of radioactivity by 50% compared with cells that were not treated with toxin.

Non-Specific Toxicity Assay

Groups of five female NIH Swiss mice were given single injections intravenously through the tail vein of escalating doses of immunotoxins as described in Example 1. Animal mortality was observed over 2 wks. The $LD_{50}$ was calculated with the Trimmed Spearman-Karbar statistical method, from the Ecological Exposure Research Division of the U.S. Environmental Protection Agency (Hamilton et al., *Environ. Sci. & Tech.*, 11: 714-719 (1977); Finney D. J., *Arch Toxicol*, 56: 215-218 (1985)).

Analysis of Liver Enzymes

Liver damage was assessed by measuring plasma enzyme activity of alanine aminotransferase (ALT), measured by ANILYTICS Inc., Gaithersburg, Md.

Stability Assay

Stability of the immunotoxins following serum treatment was determined by incubation at 0.01 mg/ml in 0.2% HSA in DPBS containing $Ca^{2+}$ and $Mg^{2+}$ at 37° C. for up to 18 hr. At each time point, the samples were frozen at –80° C. At the end of the experiment, the samples were thawed and tested for cytotoxic activity.

Antitumor Activity of Immunotoxins in Nude Mice

Antitumor activity of immunotoxins was determined in nude mice bearing human cancer cells which have appropriate antigen expression. Cells ($3 \times 10^6$) were injected subcutaneously into nude mice on day 0. Tumors approximately 0.05 $cm^3$ in size developed in animals by day 4 after tumor implantation. Starting on day 4, animals were treated with intravenous injections of each of the immunotoxins diluted in 0.2 ml of PBS/0.2% HSA. Therapy was given once every other day (on day 4, 6, and 8) and each treatment group consisted of 5 animals. Tumors were measured with a caliper every 2 or 3 days and the volume of the tumor was calculated by using the formula: tumor volume $(cm^3)$=length×(width)$^2$×0.4.

Pharmacokinetics

NIH Swiss mice were injected intravenously with 4 μg of anti-Tac(dsFv)-PE38, M1(dsFv)-PE38, M16(dsFv)-PE38, SS1(dsFv)-PE38, St6(dsFv)-PE38, or 10 μg of B3(dsFv)-PE38, Mt9(dsFv)-PE38. Blood samples were drawn at different times. The level of immunotoxin in blood was measured by a bioassay in which serum samples were incubated with human cancer antigen positive cells, and the ability of the serum sample to inhibit protein synthesis was measured. A standard curve, obtained by incubating serial dilutions of the injected toxins on antigen positive cells, was used to determine the toxin concentration in each serum sample. Pharmacokinetic parameters were calculated using an exponential curve fitting program, RSTRIP (microMath Scientific Software, Salt Lake City, Utah).

Statistical Analysis

Values are expressed as mean±SD. For comparison between the two experimental groups Student's t test was used. $p<0.05$ was considered statistically significant. The relationship was calculated using non-linear least square regression.

Example 5

This Example sets forth the results of some of the studies on M1(dsFv)-PE38 and on recombinant immuntoxins modified by the teachings herein.

Conversion of M1(scFv)-PE38 to M1(dsFv)-PE38

As discussed in Examples 1-3, above, the pI of anti-Tac (scFv)-PE38 was mutated by selective mutation of surface residues to form the immunotoxin termed M1(scFv)-PE38. These mutations lowered the pI of the immunotoxin from 10.21 to 6.82, and resulted in a 3-fold decrease in animal toxicity and hepatic necrosis. See, Examples 1-3. For clinical purposes, it is preferable to stabilize the Fv portion of the immunotoxin by replacing the peptide linking VH and VL with a disulfide bond that is introduced in the framework region. Therefore, M1(scFv)-PE38 was converted into M1(dsFv)-PE38; studies showed that M1(dsFv)-PE38 had the same toxicity in mice as its single-chain counterpart ($LD_{50}$=1.22 mg/kg, Table VII).

Identification of Mutation Sites in the Framework Region of Fv

In the mouse model discussed in Examples 1-3, above, the nonspecific toxicity of antiTAC(Fv)-PE38 was reduced by mutating neutral residues to acidic residues. In this study, basic and neutral residues in the framework regions were mutated to acidic or neutral residues. To identify residues which were candidates for mutation, the frequencies of the amino acids that occur at each position of the Fv using the Kabat database was calculated and ranked according to their frequency (Chowdhury et al., *J Molec Biol*, 281: 917-928 (1998)), as shown in the "Percent Frequency" tables of FIG. 2. Models were also created based on other Fv crystal structures to determine which residues were exposed at the surface and which residues interacted with others. With this information, the following procedure was devised to identify the positions which should be changed:

1) Align the VL and VH sequences with the Kabat database frequency table so that each amino acid residue of the Fv corresponds to a position on the Kabat sequence for the VL and VH chains, respectively.
2) Exclude as candidates for mutation residues in the CDRs.
3) Exclude as candidates for mutation residues which are already acidic.
4) Exclude residues which show 100% conservation according to the frequency table.
5) Exclude positively charged residues at positions which the "Percent Frequency" table shows are never occupied with a neutral or an acidic amino acid, and exclude neutral residues at positions which the table shows are never occupied by an acide amino acid.
6) Exclude residues with less than 30% of maximum surface area exposed.
7) Exclude residues which interact with others.
8) The remaining candidate residues may be mutated to an acidic or a neutral residue. The choice of whether to mutate to an acidic residue or a neutral one is made by referring to the Percent Frequency table. If an acidic residue is more commonly present at that Kabat position than a neutral residue, than an acidic residue is substituted; if a neutral residue is more frequently present, than a neutral residue is substituted.
9) Residues in the carboxy termini of either chain may be mutated to acidic residues.

Using the above procedure, candidates for mutation for M1, SS1 and B3 were developed as shown in Table VII. The effects of the change in pI on the electrostatic potential of the surface of the Fvs were examined using models built in the course of the studies reported in Examples 1-3. The electrostatic potential was mapped to the molecular surface of the three mutant models. It was evident from the mapping that large parts of positive potential in the lower pI mutants were decreased.

Expression and Purification of Disulfide-Bond Stabilized Fv Recombinant Immunotoxins All the mutations were confirmed by DNA sequencing and the recombinant proteins were expressed in *E. coli*, where they all accumulated in inclusion bodies. All immunotoxins were purified by a standard method, which consists of ion-exchange and size-exclusion chromatography using renatured inclusion body protein. Each of 6 immunotoxins (3 mutants and 3 wild type) eluted as a monomer upon TSK gel-filtration chromatography and migrated as a single, major band of about 63 kDa in SDS-PAGE (FIG. 3).

Isoelectric Focusing of Immunotoxins

The immunotoxins along with pI marker proteins were subjected to acrylamide gel IEF to compare their pIs. The pIs of the focusing proteins were determined from the slope of pI markers that covered a range of pI 4.5 to 9.6. The pI of M1(dsFv)-PE38, M16(dsFv)-PE38, SS1(dsFv)-PE38, St6 (dsFv)-PE38, B3(dsFv)-PE38 and Mt9(dsFv)-PE38 were 5.0, 4.8, 5.2, 5.0, 5.1 and 4.9, respectively (FIG. 4). These pI values were correlated to the pI values calculated. In several cases, more than one band was noted, probably due to the loss of one or two charged residues and possibly due to deamination.

Cytotoxicity of Mutants with Lowered pIs

The data in Table VIII shows the activity of each of the mutant molecules tested on the appropriate antigen positive target cells. Each of the mutant acidic molecules constructed had the same activity on their respective target cells as did the parental molecule. For example, on ATAC4 cells, the $IC_{50}$ of M1(dsFv)-PE38 and M16(dsFv)-PE38 was 0.04 ng/ml and on HUT102 cells was 0.1 ng/ml. Therefore, by lowering the pI of the Fv, there was no loss of specific cytotoxic activity on the target cell.

Non-Specific Toxicity of Immunotoxins

Each of these molecules was then evaluated for its nonspecific toxicity in mice (Table VII). Groups of five or more mice were injected singly with varying doses of immunotoxin and observed for 2 weeks. $LD_{50}$s were calculated with the Trimmed Spearman-Karbar statistical method. Almost all of the deaths occurred within 72 h after treatment. In general, the molecules with lower pIs were less toxic than wild type molecules. When mutations were introduced into M1(dsFv)-PE38 to produce M16(dsFv)-PE38, the Fv of which has a pI of 4.42, the single dose toxicity in mice was greatly diminished; the $LD_{50}$ rose from 1.22 mg/kg to 2.52 mg/kg. The Fv of St6(dsFv)-PE38 has a pI of 4.67. The animal toxicity ($LD_{50}$) of St6(dsFv)-PE38 is 1.85 mg/kg. Thus, it is less toxic than the starting molecule SS1(dsFv)-PE38-($LD_{50}$=0.75 mg/kg). The Fv of Mt9(dsFv)-PE38 has a pI of 4.74 compared to pI 8.96 for the Fv of B3(dsFv)-PE38. The $LD_{50}$ of Mt9(dsFv)-PE38 is 2.29 mg/kg, whereas the $LD_{50}$ of B3(dsFv)-PE38 is 0.97 mg/kg. Lowering the pI of the Fv also lowers the pI of the whole immunotoxin. The values are shown in Table VII. A plot of the pI of each of the immunotoxins against animal toxicity is shown in FIG. 7. It is evident that there is a strong correlation between the pI of the immunotoxin and the $LD_{50}$ (toxicity) in mice (r=−0.9691, p=0.0014).

Liver Toxicity of Immunotoxins

To determine the cause of death in mice, we collected blood samples 3 hr and 24 hr after administration of 18 µg of M1(dsFv)-PE38, M16(dsFv)-PE38, SS1(dsFv)-PE38, St6(dsFv)-PE38, B3(dsFv)-PE38 or Mt9(dsFv)-PE38. As shown in Table IX, there is a large increase in the level of plasma ALT after administration of M1(dsFv)-PE38, SS1(dsFv)-PE38 and B3(dsFv)-PE38. However there is little change in the plasma level of ALT after injection of the same dose of the molecules with lower pIs.

Stability of Immunotoxins

Changes in the framework region could affect the stability of the immunotoxins. Therefore, stability was examined by incubating each immunotoxin at 37° C. for 6 and 18 hr. M1(dsFv)-PE38 has good stability at 37° C. As shown in Table X, after 18 hr in PBS/0.2% HSA at 37° C., M1(dsFv)-PE38 retained more than 60% of its cytotoxic activity. M16(dsFv)-PE38 has a stability similar to M1(dsFv)-PE38. SS1(dsFv)-PE38 retained more than 80% of cytotoxic activity after 18 hr in PBS/0.2% HSA at 37° C. and St6(dsFv)-PE38 was equally stable. B3(dsFv)-PE38 retained more than 70% of its cytotoxic activity and Mt9(dsFv)-PE38 also retained more than 70% of its cytotoxic activity after 18 h. Thus, the framework mutations had very little effect on stability of the dsFv immunotoxins.

Antitumor Activity of Immunotoxins

To evaluate the antitumor activity of the anti-Tac immunotoxins, ATAC4 tumor cells were implanted subcutaneously on day 0 in mice and intravenous therapy was initiated on day 4 using increasing doses of M1(dsFv)-PE38 or M16(dsFv)-PE38. Each agent was given every other day for three doses. Typical tumor regression results are shown in FIG. 3 for mice treated with increasing doses of M16(dsFv)-PE38. Table XI shows the toxicity at each dose level and a summary of tumor responses. The data confirm that M16(dsFv)-PE38 is much less toxic to mice than M1(dsFv)-PE38. With M1(dsFv)-PE38 3 of 10 mice died at 0.75 mg/kg×3. In contrast, there were no deaths with M16(dsFv)-PE38 at 0.75 mg/kg×3. Thus, the three-dose toxicity results in nude mice confirm the one-dose study in normal mice showing that M16(dsFv)-PE38 is much less toxic than M1(dsFv)-PE38. The effect of the two immunotoxins on tumor size is also shown in Table XI. The molecules were equally active, producing 4 of 5 and 3 of 5 complete regressions (CRs) at 0.075 mg/kg×3 doses, 7 of 10 and 8 of 10 CRs at 0.15 mg/kg×3 doses, 9 of 10 and 9 of 10 CRs at 0.3 mg/kg×3 doses, and 10 of 10 and 9 of 10 CRs at 0.45 mg/kg×3 doses. At the dose levels where M1(dsFv)-PE38 caused death, M16(dsFv)-PE38 produced 10 of 10 CRs (0.75 mg/kg×3). These data clearly show the usefulness of being able to give higher doses of immunotoxins.

To evaluate antitumor activity of anti-mesothelin immunotoxins, A431-K5 cells were injected subcutaneously into mice. The method of treatment was the same as with the anti-Tac immunotoxins. Typical tumor regression results are illustrated in FIG. 3 for mice treated with increasing doses of St6(dsFv)-PE38. The data in Table XI also show the toxicity at each dose level and a summary of tumor responses. The data confirm that St6(dsFv)-PE38 is much less toxic to mice than SS1(dsFv)-PE38. When SS1(dsFv)-PE38 was administered, 2 of 10 mice died at 0.4 mg/kg×3 and 3 of 5 died at 0.6 mg/kg×3. In contrast, there were no deaths with St6(dsFv)-PE38 at these doses. The effect of the two immunotoxins on tumor size is also shown in Table XI. The molecules were equally active at the 0.2 mg/kg×3, producing 3 of 10 and 2 of 10 CRs. At the dose levels where SS1(dsFv)-PE38 caused death, St6(dsFv)-PE38 produced 3 of 10 CRs (0.4 mg/kg×3), and 6 of 10 CRs (0.6 mg/kg×3).

Finally, in order to measure the antitumor activity of anti-Lewis$^Y$ immunotoxins, mice were implanted on day 0 with A431 tumor cells and intravenous therapy was initiated on day 4 using increasing doses of Mt9(dsFv)-PE38 or B3(dsFv)-PE38. The treatment protocol was the same as described above with regard to M16(dsFv)-PE38 and St6(dsFv)-PE38). Typical tumor regression results are illustrated in FIG. 5C, which is shown for mice treated with increasing doses of Mt9(dsFv)-PE38. The data in Table XI shows the toxicity at each dose level and a summary of tumor regressions. The molecules were equally active at the 0.15 mg/kg×3 and 0.2 mg/kg×3 doses, producing 1 of 5 and 1 of 5 CRs at the lower dose, and 5 of 5 and 5 of 5 CRs at the higher dose, respectively.

Pharmacokinetics of Immunotoxins

In order to gain information on the mechanism of reduced nonspecific toxicity of lower pI mutants, the pharmacokinetic properties were examined. NIH Swiss mice were injected i.v. with a single dose of 5 µg of M1(dsFv)-PE38, M16(dsFv)-PE38, SS1(dsFv)-PE38, or St6(dsFv)-PE38 or a single dose of 10 µg of B3(dsFv)-PE38 or Mt9(dsFv)-PE38. Blood samples were drawn at different times after the injection of immunotoxins. The level of immunotoxin in the blood was measured by a bioassay in which serum samples were incubated with human cancer antigen positive cells (ATAC4 for anti-Tac immunotoxins, A431-K5 for anti-mesothelin immunotoxins, and A431 for anti-Lewis$^Y$ immunotoxins), and the ability of the serum samples to inhibit protein synthesis was measured. Results are the average of samples of 4 or 5 animals for each time point±SE (FIG. 6).

The plasma half-life of the M1(dsFv)-PE38 (pI=5.27) was about 16.8 min (Table XII) whereas the half-life of M16(dsFv)-PE38, which has a pI of 4.69, was about 9.4 min. Thus, lowering the pI of anti-Tac immunotoxin has a significant effect on half-life.

Next, the plasma half-life of SS1(dsFv)-PE38 (pI=5.61) was measured and found to be 23.9 min. In contrast, the half-life of St6(dsFv)-PE38 (pI=4.94) was 12.6 min. The data with the anti-mesothelin immunotoxins also show that lowering of the pI shortens the half-life.

The plasma half-life of B3(dsFv)-PE38 (pI=5.26) was 15.9 min, and the half-life of Mt9(dsFv)-PE38 (pI=4.83) was 13.4 min. This data also shows that lowering the pI of this immunotoxin shortened the half-life, but that the effects were less dramatic. A reduction of plasma half-life is strongly associated with a reduction of pI of the immunotoxins (r=0.9610, p=0.0023).

Example 6

In Examples 1-3, the non-specific toxicity of the recombinant single-chain immunotoxin, anti-Tac(scFv)-PE38, was reduced by introducing mutations in the Fv portion that lowered the pI of the Fv from 10.21 to 6.82. This was accomplished without altering residues in the complementarily-determining regions, and therefore did not affect the specific cytotoxic effect of the immunotoxin on target cells. As a consequence, tumor bearing mice could be treated with higher doses and obtain enhanced antitumor activity. Most of the changes were from neutral to acidic residues and only one immunotoxin was studied.

These findings have been extended in Examples 4-6 to three different immunotoxins and by changing many basic residues to neutral or acidic residues, using as a guide the consensus sequence of residues in the framework regions (Chowdhury et al., *J. Molecular Biol*, 281: 917-928 (1998)). Many residues are highly conserved and these were not changed because such mutations might affect Fv folding or stability. Immunotoxins in which the Fvs were connected by a disulfide bond linking between VH and VL were studied, since these molecules are more stable and better suited for patient use (Reiter et al., *Nature Biotechnology*, 14:1239-1245 (1996)). The changes resulted in an improvement of the $LD_{50}$ of the anti-Tac immunotoxin in mice, from 0.34 mg/kg for anti-Tac(scFv)-PE38 (the immunotoxin is now in clinical trials) to 2.52 mg/kg for M16(dsFv)-PE38. This 7-fold decrease in mouse toxicity predicts that, in humans, the response to immunotoxins developed against CD25 which have already shown good antitumor activity in patients with leukemias or lymphomas (Kreitman et al., *J. Of Clinical Oncology*, 18: 1622-1636 (2000)) will be greatly increased.

With each of the 3 immunotoxin pairs studied, the decrease in animal toxicity caused by a lowering of the pI was more than 2-fold. FIG. 7 shows that the correlation between $LD_{50}$ and pI is statistically significant (r=−0.9691, p=0.0014).

The mechanism by which immunotoxin anti-Tac(scFv)-PE38 produces toxicity in mice was also analyzed. TNFα produced by Kupffer cells turned out to play an important role in causing hepatocyte damage. It was previously reported that charged molecules can affect the release of TNFα by macrophages (Yui et al., *Japanese J. Cancer Research*, 82: 1028-1034 (1991)). Without wishing to be bound by theory, it is possible that macrophages bind fewer negatively charged immunotoxin molecules than positively charged molecules and consequently release less TNFα, which is toxic to hepatocytes.

In order to clarify the cause of decreasing nonspecific toxicity by lowering pI of Fv, pharmacolinetic properties of exemplary immunotoxins with lowered pI were studied. It was observed that molecules with a lower pI were more rapidly cleared from the circulation, even though their antitumor activity was not altered. It is possible that tumor uptake is increased or distribution of the immunotoxin in the tumor is more efficient when the pI is lowered and this compensates for the more rapid clearance which should by itself decrease antitumor activity. The cationic Fab undergo a charge interaction with the proximal tubuls and are reabsorbed. On the other hand the anionic Fab, due to charge differences, are not as effectively absorbed into the proximal tubule (Kobayashi, H, et al., *Cancer Research*, 59:422-430 (1999)). Therefore a larger fraction is excreted in the urine. Deceased interaction with proximal tubules which are charged negative, could account for the more rapid clearance of the immunotoxin from the circulation. The correlation between plasma half-life and pI was highly significant statistically (r=0.9610, p=0.0023).

Several investigators have shown that when an antibody, Fv, or Fab are anionized by the acylation of the epsilon amino group of lysine residues or by the addition of amino acids to the carboxy terminus, pharmacokinetic properties are altered (Tenkate, C., et al., *European J. Nuclear Medicine*, 17:305-309 (1990); Pavlinkova, G., et al., *Nuclear Medicine and Biology*, 26:27-34 (1999); Kobayashi, H., et al., *Cancer Research*, 59:422-430 (1999); Kim, I., et al., *Bioconjugate Chemistry*, 10:447-453 (1999)). Some reports have shown that lowering the pI increased clearance from the circulation, while other reports showed that lowering the pI decreased clearance. The strategy of the current work, reducing the pI by mutating specific framework residues, is different from the approach used in other studies, in which the properties of the proteins are grossly and often unpredictably altered. Although the modified antibodies of other studies often had a decrease in immunoreactivity (specific binding to target molecules), the molecules in the current study with lower pIs actually have the same immunoreactivity as the parental molecules.

In summary, the studies herein show that the nonspecific toxicity of immunotoxins can be altered by selectively mutating residues in the framework regions to decrease the pI of the immunotoxin. Studies with three different immunotoxins, M1(dsFv)-PE38, SS1(dsFv)-PE38, and B3(dsFv)-PE38, targeted to three different target antigens, demonstrated that toxicity can be decreased by more than 2-fold without decreasing the specific cellular toxicity or antitumor activity of an immunotoxin.

Example 7

This Example sets forth DNA sequences encoding the VL and VH chains of the M16, St6, and Mt9 Fvs. Persons of skill in the art will appreciate that due to the degeneracy of the genetic code, a large number of other nucleic acid sequences could be constructed which would encode the same amino acid sequences as are encoded by the following exemplary sequences.

```
SEQ ID NO:15: M16-VL
GACATCGAACTCACCCAGTCTCCAGCAATCATGTCTGCATCTCCAGGGGAGCAAG

TCACCATAACCTGCAGTGCCAGCTCAAGTATAAGTTACATGCACTGGTTCCAGCA

GAAGCCAGGCACTTCTCCCCAGCTATGGATTTATACCACATCCAACCTGGCTTCT

GGAGTCCCTGCTCGCTTCAGTGGCAGTGGATCCGGGACCGATTACTCTCTCACAA
```

-continued

TTTCGAATATGGAGGCTGAAGATGCTGCCACTTATTACTGCCATCAAAGGAGTAC

TTACCCACTCACGTTCGGTTGCGGGACCGAGCTGGAACTCGAA

SEQ ID NO:16: M16-VH
GAGGTCCAACTGGTGGAGTCTGGGGCTGAGCTCGCAGAACCTGGGGCCTCAGTG

AAGATGTCCTGCAAGGCTTCTGGCTACACCTTTACTAGCTACAGGATGCACTGGG

TAAAACAGAGGCCTGAACAGTGTCTGGAATGGATTGGATATATTAATCCTAGCA

CTGGGTATACTGAATACAATCAGAAGTTCAAGGACAAGGCCACATTGACTGCAG

ACGATTCCTCCAGTACTGCCTACATGCAACTGAGCAGCCTGACATTTGAGGACTC

TGCAGTCTATTACTGTGCAAGAGGGGGGGGGTCTTTGACTACTGGGGCCAAGG

AACCACTCTCACAGTCTCCTCC

SEQ ID NO:17: St6-VL
ATGGACATCGAGCTCACTCAGGATCCAGCAATCATGTCTGCATCTCCCGGGGAGC

AGGTCACCATGACCTGCAGTGCCAGCTCAAGTGTAAGTTACATGCACTGGTACCA

GCAGAAGTCAGGCACCTCCCCCAAAAGATGGATTTATGACACATCCAAACTGGC

TTCTGGAGTCCCCGATCGCTTCAGTGGCAGTGGGTCTGGAAACTCTTACTCTCTC

ACAATCAGCAGCGTGGAGGAGGAAGATGATGCTACGTATTACTGCCAGCAGTGG

TCCAAGCACCCTCTCACGTTCGGTTGCGGGACAAAGCTTGAAATAGAA

SEQ ID NO:18: St6-VH
GAGGTACAACTGCAGCAGTCTGGGCCTGAGCTCGAGCAGCCTGGCGCTTCAGTG

AAGTTATCCTGCAAGGCATCTGGTTACTCATTCACTGGCTACACCATGAACTGGG

TGAAGCAGAGTCATGGAAAGTGCCTTGAGTGGATTGGACTTATTACTCCTTACAA

TGGTGCTTCTAGCTACAACCAGAAGTTCAGGGGCAAGGCCACATTAACTGTAGA

CAAGTCACAAAGTACTGCCTACATGGACCTCCTCAATCTGACAAATGAAGACTCT

GCAGTCTATTTCTGTGCAAGGGGGGGTTACGACGGGAGGGGTTTTGACTACTGGG

GCCAAGGGACCACGGTCACCGTCTCCTCA

SEQ ID NO:19: Mt9-VL
GACGTGGAGATGACCCAGTCTCCATTGAGTTTACCTGTCAGTCTTGGAGATCAAG

CCTCCATCTCTTGCAGATCTAGTCAGATCATTGTACATAGTAATGGAAACACCTA

TTTAGAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGA

CAGATTTCACACTCACCATCAGCAGTGTGGAGGCGGAGGATCTGGGAGTTTATTA

CTGCTTTCAAGGTTCACATGTTCCATTCACGTTCGGCTGTGGGACAGATCTGGAA

ATAGAT

SEQ ID NO:20: Mt9-VH
GATGTGAAGCTGGTGGAGTCTGGGGGAGGCTTAGTGCAGCCTGGAGGGTCCCTG

AAACTCTCCTGTGCAACCTCTGGATTCACTTTCAGTGACTATTACATGTATTGGGT

TCGCCAGACTCCAGAGAAGTGTCTCGAGTGGGTCGCATACATTAGTAATGATGAT

AGTTCCGCCGCTTATTCAGACACTGTAAAGGGCCGGTTCACCATCTCCAGAGACA

ATGCCAGGAACACCCTCTACCTGCAAATGAGCCGTCTGAAGTCTGAGGACACAG

CCATATATTACTGCGCAAGAGGACTGGCCTGGGGAGCCTGGTTTGCTTACTGGGG

CCAAGGGACTCTGGTCACTGTCTCC

TABLE VII

Immunotoxin mutations, pIs and $LD_{50}s$

| Immunotoxins | Mutations of FV | pI OF Fv[1] | pI of IT[1] | $LD_{50}$ (mg/kg)[2] | 95% confidence of $LD_{50}$[2] |
|---|---|---|---|---|---|
| M1(dsFv)-PE38[3] | (VH: Q1E, H3Q, Q5V, Q6E, G42E) + (VL: Q1D, V3E, S70D) | 7.76 | 5.27 | 1.22 | 1.14-1.31 |
| M16(dsFv)-PE38 | dsM1 + (VH: K13E, K73D) + (VL: K18Q, K45Q, R77N, K103E, K107E) | 4.42 | 4.69 | 2.52 | 2.22-2.85 |
| SS1(dsFv)-PE38 | none | 9.46 | 5.61 | 0.75 | 0.59-0.95 |
| St6(dsFv)-PE38 | (VH: Q1E, K13Q, S75Q, S84N, S(82B)N) + 4.67(VL: S7D, K18Q, G60D, A80E, K107E) | 4.67 | 4.94 | 1.85 | |
| B3(dsFv)-PE38 | none | 8.96 | 5.26 | 0.97 | 0.84-1.10 |
| Mt9(dsFv)-PE38 | (VL: L3E, K74T, R77S, K103D, K107D) | 4.74 | 4.83 | 2.29 | 1.93-2.72 |

[1]pI of Fv and pI of entire immunotoxin (IT) was calculated using a program in the Genetics Computer Group (Madison, WI)
[2]Groups of more than 5 female NIH Swiss mice were given injections intravenously once through the tail vein. The $LD_{50}$ is calculated with Trimmed Spearman-Karbar statistical method.
[3]M1(dsFv)-PE38 is a mutant form of anti-Tac(dsFv)-PE38.

TABLE VIII

Cytotoxic activity of wild type immunotoxins and lower pI mutants

A) anti-Tac immunotoxins

| | | IC50 (NG/ML) | |
|---|---|---|---|
| CELLS | TYPE | M16(DSFV)-PE38 | M1(DSFV)-PE38 |
| ATAC4 | Epidermoid | 0.04 ± 0.01 | 0.04 ± 0.01 |
| HUT102 | ATL | 0.1 ± 0.02 | 0.1 ± 0.02 |
| Raji | Burkitt's Lymphoma | >1000 | >1000 |
| OHS | Osteosarcoma | >1000 | >1000 |

B) anti-mesothelin immunotoxins

| | | IC50 (NG/ML) | |
|---|---|---|---|
| CELLS | TYPE | SS1(DSFV)-PE38 | ST6(DSFV)-PE38 |
| A431-K5 | Epidermoid | 0.63 ± 0.06 | 0.53 ± 0.07 |

C) anti-LewisY immunotoxins

| | | IC50 (NG/ML) | |
|---|---|---|---|
| CELLS | TYPE | B3(DSFV)-PE38(LMB9) | MT9(DSFV)-PE38 |
| A431 | Epidermoid | 0.43 ± 0.05 | 0.51 ± 0.04 |

TABLE IX

PLASMA ALT LEVELS IN MICE TREATED WITH IMMUNOTOXINS[1]

| | Plasma ALT (U/L)[2] after injection of ITs | |
|---|---|---|
| Immunotoxins | 3 hr | 24 hr |
| M1(dsFv)-PE38 | 30 ± 5.7 | 256 ± 248 |
| M16(dsFv)-PE38 | 28 ± 20 | 61 ± 43 |
| SS1(dsFv)-PE38 | 19 ± 4.2 | 4762 ± 2058 |
| St6(dsFv)-PE38 | 28 ± 25 | 127 ± 56 |
| B3(dsFv)-PE38 | 37 ± 19 | 6338 ± 1934 |
| Mt9(dsFv)-PE38 | 38 ± 35 | 113 ± 12 |

[1]Data are expressed as the mean ± SD (n = 4)
[2]Normal range of plasma ALT is less than 150 U/L

TABLE X

Stability of wild type and lowered pI mutants.

| | IC50 (ng/ml)$^a$ after incubation in PBS/0.2% HSA at 37° C. | | |
|---|---|---|---|
| ITs | 0 | 6 | 18 (h |
| M1(dsFv)-PE38 | 0.04 ± 0.01 | 0.05 ± 0.02 | 0.06 ± 0.02 |
| M16(dsFv)-PE38 | 0.04 ± 0.01 | 0.06 ± 0.02 | 0.08 ± 0.02 |
| SS1(dsFv)-PE38 | 0.63 ± 0.10 | 0.64 ± 0.10 | 0.78 ± 0.10 |
| St6(dsFv)-PE38 | 0.53 ± 0.10 | 0.58 ± 0.10 | 0.58 ± 0.10 |
| B3(dsFv)-PE38 | 0.43 ± 0.10 | 0.59 ± 0.07 | 0.60 ± 0.10 |
| Mt9(dsFv)-PE38 | 0.51 ± 0.09 | 0.64 ± 0.05 | 0.71 ± 0.10 |

$^a$Data are expressed as the mean ± SD (n = 3)

TABLE XI

Effect of increasing doses of immunotoxins on toxicity and tumor response in mice

| | Death/Total[1] | PR[2] | CR[2] |
|---|---|---|---|
| M1(dsFv)-PE38 | | | |
| 0.075 mg/kg × 3 | 0/5 | 5/5 | 3/5 |
| 0.15 mg/kg × 3 | 0/10 | 10/10 | 8/10 |
| 0.3 mg/kg × 3 | 0/10 | 10/10 | 9/10 |
| 0.45 mg/kg × 3 | 0/10 | 10/10 | 9/10 |
| 0.75 mg/kg × 3 | 3/10 | 7/7[3] | 7/7[3] |

TABLE XI-continued

Effect of increasing doses of immunotoxins on toxicity and tumor response in mice

|  | Death/Total[1] | PR[2] | CR[2] |
|---|---|---|---|
| M16(dsFv)-PE38 | | | |
| 0.075 mg/kg × 3 | 0/5 | 5/5 | 4/5 |
| 0.15 mg/kg × 3 | 0/10 | 10/10 | 7/10 |
| 0.3 mg/kg × 3 | 0/10 | 10/10 | 9/10 |
| 0.45 mg/kg × 3 | 0/10 | 10/10 | 10/10 |
| 0.75 mg/kg × 3 | 0/10 | 10/10 | 10/10 |
| SS1(dsFv)-PE38 | | | |
| 0.2 mg/kg × 3 | 0/10 | 10/10 | 2/10 |
| 0.4 mg/kg × 3 | 2/10 | 8/8[3] | 2/8[3] |
| 0.6 mg/kg × 3 | 3/5 | 2/2[3] | 0/2[3] |
| St6(dsFv)-PE38 | | | |
| 0.2 mg/kg × 3 | 0/10 | 10/10 | 3/10 |
| 0.4 mg/kg × 3 | 0/10 | 10/10 | 3/10 |
| 0.6 mg/kg × 3 | 0/10 | 10/10 | 6/10 |
| B3(dsFv)-PE38 | | | |
| 0.05 mg/kg × 3 | 0/5 | 5/5 | 0/5 |
| 0.1 mg/kg × 3 | 0/5 | 5/5 | 0/5 |
| 0.15 mg/kg × 3 | 0/5 | 5/5 | 1/5 |
| 0.2 mg/kg × 3 | 0/5 | 5/5 | 5/5 |
| Mt9(dsFv)-PE38 | | | |
| 0.05 mg/kg × 3 | 0/5 | 5/5 | 0/5 |
| 0.1 mg/kg × 3 | 0/5 | 5/5 | 0/5 |
| 0.15 mg/kg × 3 | 0/5 | 5/5 | 1/5 |
| 0.2 mg/kg × 3 | 0/5 | 5/5 | 5/5 |
| 0.2 ml PBS/0.2% HSA × 3 | 0/50 | 0/50 | 0/50 |

[1]Number of mice that died divided by number injected.
[2]CR, complete regression of tumor for a minimum of 4 days; PR, reduction of the sum of the tumor length and width by >50% of pre-treatment values;
[3]Dead mice could not be evaluated.

TABLE XII

Pharmacokinetics of immunotoxins

| Immunotoxins | pI of IT | T1/2(min) | AUC(ng min/ml)[a] |
|---|---|---|---|
| M1(dsFv)-PE38 | 5.27 | 16.8 | 324424 |
| M16(dsFv)-PE38 | 4.69 | 9.4 | 260909 |
| SS1(dsFv)-PE38 | 5.61 | 23.9 | 387350 |
| St6(dsFv)-PE38 | 4.94 | 12.6 | 237591 |
| B3(dsFv)-PE38 | 5.26 | 15.9 | 136927 |
| Mt9(dsFv)-PE38 | 4.83 | 13.4 | 110691 |

[a]Calculated by RSTRIP

While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited herein are incorporated by reference in their entirety for all purposes to the same extent as if each individual publication or patent document were so individually denoted. Citation of various references in this document is not an admission that any particular reference is considered to be "prior art" to the invention.

What is claimed is:

1. A recombinant immunotoxin comprising an antibody or antigen-binding fragment thereof comprising SEQ ID NO:3 and SEQ ID NO:10 and a toxin moiety.

2. A recombinant immunotoxin comprising an antibody or antigen-binding fragment thereof comprising SEQ ID NO:5 and SEQ ID NO:12 and a toxin moiety.

3. A recombinant immunotoxin comprising an antibody or antigen-binding fragment thereof comprising SEQ ID NO:7 and SEQ ID NO:14 and a toxin moiety.

4. A recombinant immunotoxin of any one of claims 1, 2 or 3, wherein the toxin moiety is selected from the group consisting of *Pseudomonas* exotoxin A ("PE") or a cytotoxic fragment or mutant thereof, Diphtheria toxin or a cytotoxic fragment or mutant thereof, ricin or a cytotoxic fragment thereof, abrin or a cytotoxic fragment thereof, saporin or a cytotoxic fragment thereof, pokeweed antiviral toxin or a cytotoxic fragment thereof, and bryodin 1 or a cytotoxic fragment thereof.

5. A recombinant immunotoxin of claim 4, wherein the toxin moiety is selected from the group consisting of PE38, PE35, PE40, PE4E, and PE38QQR.

6. A composition comprising a recombinant immunotoxin of claim 1 in a pharmaceutically acceptable carrier.

7. A composition comprising a recombinant immunotoxin of claim 2 in a pharmaceutically acceptable carrier.

8. A composition comprising a recombinant immunotoxin of claim 3 in a pharmaceutically acceptable carrier.

* * * * *